US011884714B2

(12) United States Patent
Perrin et al.

(10) Patent No.: US 11,884,714 B2
(45) Date of Patent: Jan. 30, 2024

(54) CYCLIC PEPTIDE ANALOGS OF MELANOCORTIN AND AMANITIN AND METHODS OF MAKING SUCH

(71) Applicants: THE UNIVERSITY OF BRITISH COLUMBIA, Vancouver (CA); PROVINCIAL HEALTH SERVICES AUTHORITY, Vancouver (CA)

(72) Inventors: David Perrin, Vancouver (CA); Mihajlo Todorovic, Vancouver (CA); François Bénard, Vancouver (CA); Chengcheng Zhang, Vancouver (CA)

(73) Assignees: THE UNIVERSITY OF BRITISH COLUMBIA, Vancouver (CA); PROVINCIAL HEALTH SERVICES AUTHORITY, Vancouver (CA)

( * ) Notice: Subject to any disclaimer, the term of this patent is extended or adjusted under 35 U.S.C. 154(b) by 0 days.

(21) Appl. No.: 17/835,770

(22) Filed: Jun. 8, 2022

(65) Prior Publication Data
US 2022/0298219 A1    Sep. 22, 2022

Related U.S. Application Data

(63) Continuation of application No. 16/804,465, filed on Feb. 28, 2020, now Pat. No. 11,396,535.

(60) Provisional application No. 62/812,410, filed on Mar. 1, 2019.

(51) Int. Cl.
| | | |
|---|---|---|
| C07K 14/685 | (2006.01) | |
| C07K 14/68 | (2006.01) | |
| C07K 5/10 | (2006.01) | |
| C07K 5/12 | (2006.01) | |
| C07K 7/56 | (2006.01) | |
| C07K 14/72 | (2006.01) | |
| A61K 38/00 | (2006.01) | |

(52) U.S. Cl.
CPC ............ C07K 14/685 (2013.01); A61K 38/00 (2013.01)

(58) Field of Classification Search
CPC ........ C07K 14/685; C07K 7/56; C07K 14/72; C07K 14/68; C07K 5/10; C07K 5/12; A61K 38/00
See application file for complete search history.

(56) References Cited

U.S. PATENT DOCUMENTS

| | | |
|---|---|---|
| 5,650,134 A | 7/1997 | Albert et al. |
| 8,039,435 B2 | 10/2011 | Dong et al. |
| 8,114,381 B2 | 2/2012 | Perrin et al. |
| 8,153,101 B2 | 4/2012 | McBride et al. |
| 8,574,546 B2 | 11/2013 | Perrin et al. |
| 8,691,761 B2 | 4/2014 | Rivier et al. |
| 10,150,804 B2 | 12/2018 | Benard et al. |
| 11,395,857 B2 | 7/2022 | Benard et al. |
| 11,396,535 B2 | 7/2022 | Perrin et al. |
| 2014/0112873 A1 | 4/2014 | Gillies et al. |
| 2014/0147381 A1 | 5/2014 | Espenan |
| 2021/0024605 A1 | 1/2021 | Perrin et al. |
| 2021/0205483 A1 | 7/2021 | Benard et al. |
| 2022/0040340 A1 | 2/2022 | Benard et al. |
| 2022/0062446 A1 | 3/2022 | Perrin et al. |
| 2022/0213138 A1* | 7/2022 | Li .............................. C07K 7/08 |

FOREIGN PATENT DOCUMENTS

| | | |
|---|---|---|
| CN | 102066974 A | 5/2011 |
| CN | 105636924 A | 6/2016 |
| CN | 106967152 A | 7/2017 |
| CN | 108699087 A | 10/2018 |
| WO | WO 2005/077967 A1 | 8/2005 |
| WO | WO 2009/012596 A1 | 1/2009 |
| WO | WO-2009135015 A2 | 11/2009 |
| WO | WO 2011/066521 A2 | 6/2011 |
| WO | WO 2012/094334 A1 | 7/2012 |
| WO | WO 2012/118909 A1 | 9/2012 |
| WO | WO 2014/134716 A1 | 9/2014 |
| WO | WO-2015055318 A1 | 4/2015 |
| WO | WO 2015/100498 A1 | 7/2015 |
| WO | WO-2021168567 A1 | 9/2021 |

OTHER PUBLICATIONS

Antunes et al., "Influence of Different Spacers on the Biological Profile of a DOTA-Somatostatin Analogue," Bioconjugate Chemistry, 2007, vol. 18, pp. 84-92.

Banerjee et al., "Clinical applications of Gallium-68," Applied Radiation and Isotopes, 2013, vol. 76, pp. 2-13.

Breeman et al., "Somatostatin receptor-mediated imaging and therapy: basic science, current knowledge, limitations and future perspectives," European Journal of Nuclear Medicine, Sep. 2001, vol. 28, No. 9, pp. 1421-1429.

Buchmann et al., "Comparison of 68Ga-DOTATOC PET and 111In-DTPAOC (Octreoscan)SPECT in patients with neuroendocrine tumours," Eur J Nucl Med Mol Imaging., 2007, vol. 34, pp. 1617-1626.

Cai et al., "RGD-based PET tracers for imaging receptor integrin αvβ3 expression," Journal of Labelled Compounds and Radiopharmaceuticals, 2013, vol. 56, pp. 264-279.

Chin et al., "First Experience with Clinical-Grade [18F]FP-P(RGD)2: An Automated Multi-step Radiosynthesis for Clinical PET Studies," Mol Imaging Biol., 2012, vol. 14, pp. 88-95.

(Continued)

*Primary Examiner* — Julie Ha
(74) *Attorney, Agent, or Firm* — COOLEY LLP

(57) ABSTRACT

The invention described herein is based in part on the discovery of a protein/peptide crosslink, which introduces fluorescent properties, and which has been applied to synthesize analogues of melanocortin and amanitin as choice peptides to be explored in the context of isoindole peptides. Without limitation, it is expected that those trained in the art of peptide synthesis and stapling would appreciate the consequences of this invention such that other peptides of varied length can be similarly constrained by isoindole staples as featured herein.

1 Claim, 10 Drawing Sheets
Specification includes a Sequence Listing.

(56) References Cited

OTHER PUBLICATIONS

Doedens et al., "Multiple N-Methylation of MT-II Backbone Amide Bonds Leads to Melanocortin Receptor Subtype hMC1R Selectivity: Pharmacological and Conformational Studies," J Am Chem Soc, 2010, vol. 132, pp. 8115-8128.

Eberl et al., "High beam current operation of a PETtrace™ cyclotron for 18F production," Applied Radiation and Isotopes, 2012, vol. 70, pp. 922-930.

Extended Search Report for European Patent Application No. 15733077.0, dated Jun. 19, 2017, 6 pages.

Extended European Search Report for European Application No. 19807462.7, dated Mar. 10, 2022, 8 pages.

Fani et al., "Unexpected Sensitivity of sst2 Antagonists to N-Terminal Radiometal Modifications," The Journal of Nuclear Medicine, Sep. 2012, vol. 53, No. 9, pp. 1481-1489.

Gabriel et al., "68Ga-DOTA-Tyr3-Octreotide PET in Neuroendocrine Tumors: Comparison with Somatostatin Receptor Scintigraphy and CT," The Journal of Nuclear Medicine, Apr. 2007, vol. 48, No. 4, pp. 508-518.

Gabriel et al., "An Intrapatient Comparison of 99mTc-EDDA/HYNIC-TOC with 111In-DTPA Octreotide for Diagnosis of Somatostatin Receptor-Expressing Tumors," The Journal of Nuclear Medicine, May 2003, vol. 44, No. 5, pp. 708-716.

Ginj et al., "Design, Synthesis, and Biological Evaluation of Somatostatin-Based Radiopeptides," Chemistry & Biology, Oct. 2006, vol. 13, pp. 1081-1090.

Guo et al., "Preparation and Biological Evaluation of 64Cu Labeled Tyr3-Octreotate using a Phosphonic Acid-Based Cross-Bridged Macrocyclic Chelator," Bioconjugate Chemistry, 2012, vol. 23, pp. 1470-1477.

Henze et al., "PET Imaging of Somatostatin Receptors Using [68GA]DOTA-D-Phe1-Tyr3-Octreotide: First Results in Patients with Meningiomas," The Journal of Nuclear Medicine, Jul. 2001, vol. 42, No. 7, pp. 1053-1056.

International Search Report and Written Opinion for International (PCT) Patent Application No. PCT/CA2015/000002, dated May 4, 2015, 10 pages.

International Search Report and Written Opinion of the International Searching Authority for International Application No. PCT/CA2019/050703, dated Jul. 17, 2019, 11 pages.

International Search Report and Written Opinion of the International Searching Authority for International Application No. PCT/CA2019/051853, dated Feb. 18, 2020, 8 pages.

Kayani "A Comparison of 68Ga-DOTATATE and 18F-FDG PET/CT in Pulmonary Neuroendocrine Tumors," The Journal of Nuclear Medicine, Dec. 2009, vol. 50, No. 12, pp. 1927-1932.

Kemerink et al., Effect of the positron range of 18F, 68Ga and 124I on PET/CT in lung equivalent materials, Eur J Nucl Med Mol Imaging, 2011, vol. 38, pp. 940-948.

Krausz et al., "SPECT/CT hybrid imaging with 111In-pentetreotide in assessment of neuroendocrine tumours," Clinical Endocrinology, 2003, vol. 59, pp. 565-573.

Kwekkeboom et al. "Peptide Receptor Radionuclide Therapy in Patients With Gastroenteropancreatic Neuroendocrine Tumors," Seminars in Nuclear Medicine, Mar. 2010, vol. 40, No. 2, pp. 78-88.

Kwekkeboom et al. "Somatostatin receptor-based imaging and therapy of gastroenteropancreatic neuroendocrine tumors," Endocr Relat Cancer., 2010, vol. 17, pp. R53-R73.

Laforest et al. "Image quality with non-standard nuclides in PET," QJ Nucl Med Mol Imaging, 2008, vol. 52, pp. 151-158.

Laverman et al., "A Novel Facile Method of Labeling Octreotide with $^{18}$F-Fluorine," The Journal of Nuclear Medicine, Mar. 2010, vol. 51(3), pp. 454-461.

Laverman et al., "Optimized labeling of NOTA-conjugated octreotide with F-18," Tumor Biol., 2012, vol. 33, pp. 427-434.

Leyton et al., "Targeting Somatostatin Receptors: Preclinical Evaluation of Novel $^{18}$F-Fluoroethyltriazole-Tyr$^3$-Octreotide Analogs for PET," The Journal of Nuclear Medicine, Sep. 2011, vol. 52(9), pp. 1441-1448.

Li et al., "One-step and one-pot-two-step radiosynthesis of cyclo-RGD-$^{18}$F-aryltrifluoroboronate conjugates for functional imaging," Am. J. Nucl. Med. Mol. Imaging, 2013, vol. 3(1), pp. 44-56.

Liu et al., ""Kit-like" radiosynthesis and biological evaluation of an F-labeled 4-(2-Aminoethyl)-benzenesulfonamide (AEBS) trimer for imaging carbonic anhydrase IX expression with positron emission tomography," World Molecular Imaging Congress, Sep. 19, 2013—poster, 1 page.

Liu et al., "(18)F-trifluoroborate derivatives of [des-arg(10)]kallidin for imaging bradykinin b1 receptor expression with positron emission tomography," Molecular Pharmaceutics, 2015, vol. 12, No. 3, pp. 974-982.

Liu et al., "An Organotrifluoroborate for Broadly Applicable One-Step 18F-Labeling," Angew Chem Int Ed., 2014, vol. 53, pp. 11876-11880.

Liu et al., "Facile synthesis and biological evaluation of an 18F-labeled 4-(2-aminoethyl) benzenesulfonamide (AEBS) trimer for imaging carbonic anhydrase IX expression with positron emission tomography," World Molecular Imaging Congress, Sep. 19, 2013, Presentation No. LBAP 029, 2 pages.

Liu et al., "Kit-like 18F-labeling of RGD-19F-Arytrifluroborate in high yield and at extraordinarily high specific activity with preliminary in vivo tumor imaging," Nuclear Medicine and Biology, vol. 40, 2013, pp. 841-849.

Liu et al., "Preclinical evaluation of a high affinity 18F-trifluoroborate octreotate derivative for somatostatin receptor imaging—poster," UBC, 2014, 1 page.

Liu et al., "Preclinical Evaluation of a High-Affinity $^{18}$F-Trifluoroborate Octreotate Derivative for Somatostatin Receptor Imaging," Journal of Nuclear Medicine, Sep. 2014, vol. 55(9), pp. 1499-1505.

Liu et al., "Preclinical Evaluation of a Novel 18F-Labelled Somatostatin Receptor-Binding Peptide—Abstract Proof," ScholarOne, Inc., 2014, Control ID: 1931699, 4 pages.

Liu et al., "Preclinical evaluation of a novel F-labelled somatostatin receptor-binding peptide," The Journal of Nuclear Medicine, 2014, vol. 55 (Supplement 1): 1089, 1 page.

Liu et al., "Rapid, one-step, high yielding 18F-labeling of an aryltrifluoroborate bioconjugate by isotope exchange at very high specific activity," Journal of Labelled Compounds and Radiopharmaceuticals, 2012, vol. 55, pp. 491-496.

Liu et al., "Stoichiometric Leverage: Rapid 18F-Aryltrifluoroborate Radiosynthesis at High Specific Activity for Click Conjugation," Angew. Chem. Int. Ed., 2013, vol. 52, pp. 2303-2307.

Matteson et al., "Iodomethaneboronic Esters and Aminomethaneboronic Esters," Journal of Organometallic Chemistry, 1979, vol. 170, pp. 259-264.

Means et al., "Chemical Modifications of Proteins: History and Applications," Bioconjugate Chemistry, 1990, vol. 1, No. 1, pp. 2-12.

Poeppel et al., "$^{68}$GA-DOTATOC Versus $^{68}$Ga-DOTATATE PET/CT in Functional Imaging of Neuroendocrine Tumors," The Journal of Nuclear Medicine, Dec. 2011, vol. 52(12), pp. 1864-1870.

Poethko et al., "Two-Step Methodology for High-Yield Routine Radiohalogenation of Peptides: 18F-Labeled RGD and Octreotide Analogs," The Journal of Nuclear Medicine, May 2004, vol. 45 No. 5, pp. 892-902.

Pourghisian et al., "(18)F-AmBF3-MJ9: a novel radiofluorinated bombesin derivative for prostate cancer imaging," Bioorganic & Medicinal Chemistry, 2015, vol. 23, No. 7, pp. 1500-1506.

Reubi et al., "Affinity profiles for human somatostatin receptor subtypes SST1-SST5 of somatostatin radiotracers selected for scintigraphic and radiotherapeutic use," European Journal of Nuclear Medicine, Mar. 2000, vol. 27, No. 3, pp. 273-282.

Roxin et al. "Preliminary evaluation of 18F-labeled LLP2A-trifluoroborate conjugates as VLA-4 (α4β1 integrin) specific radiotracers for PET imaging of melanoma" Nuclear Medicine and Biology 61 (2018) 11-20.

Roxin et al., "A metal-free DOTA-conjugated $^{18}$F-labeledradiotracer: [$^{18}$F]DOTA-AMBF$_3$ LLP2A for imaging VLA-4 Over-expression in murine melanoma with improved tumor uptake and greatly enhanced renal clearance," Bioconjugate Chem. 2019, 30, 1210-1219.

(56) References Cited

OTHER PUBLICATIONS

Sprague et al., "Preparation and Biological Evaluation of Copper-64-Labeled Tyr3-Octreotate Using a Cross-Bridged Macrocyclic Chelator," Clinical Cancer Research, Dec. 2004, vol. 10, pp. 8674-8682.
Storch et al., "Evaluation of [99mTc/EDDA/HYNIC0]Octreotide Derivatives Compared with [111In- DOTA0, Tyr3, Thr8]Octreotide and [111In-DTPA0]Octreotide: Does Tumor or Pancreas Uptake Correlate with the Rate of Internalization?" The Journal of Nuclear Medicine, Sep. 2005, vol. 46, No. 9, pp. 1561-1569.
Vallabhajosula et al., "Preclinical Evaluation of Technetium-99m-Labeled Somatostatin Receptor-Binding Peptides," The Journal of Nuclear Medicine, Jun. 1996, vol. 37, No. 6, pp. 1016-1022.
Virgolini et al. "Somatostatin Receptor Subtype Specificity and in Vivo Binding of a Novel Tumor Tracer. 99mTc-P8291," Cancer Research, May 1998, vol. 58, pp. 1850-1859.
Wängler et al., "One-Step $^{18}$F-Labeling of Carbohydrate-Conjugated Octreotate-Derivatives Containing a Silicon-Fluoride-Acceptor (SiFA): In Vitro and in Vivo Evaluation as Tumor Imaging Agents for Positron Emission Tomography," Bioconjugate Chem., 2010, vol. 21(12), pp. 2289-2296.
Wester et al., "PET imaging of somatostatin receptors: design, synthesis and preclinical evaluation of a novel 18F-labelled, carbohydrated analogue of octreotide," European Journal of Nuclear Medicine and Molecular Imaging, Jan. 2003, vol. 30, No. 1, pp. 117-122.
Zhan et al., "Hydration of the Fluoride Anion: Structures and Absolute Hydration Free Energy from First-Principles Electronic Structure Calculations," J Phys Chem A., 2004, vol. 108, pp. 2020-2029.
Zhang et al., "Preclinical Melanoma Imaging with $^{68}$Ga-labeled α-Melanocyte-Stimulating Hormone Derivatives Using PET," Theranostics, 2017, vol. 7, Issue 4, pp. 805-813.
Zhang et al., "Selectively targeting the melanocortin-1 receptor with N-methylation of an αMSH derivative for PET imaging of melanoma," Journal of Nuclear Medicine, May 2018, 59 (Supplement 1): 611.
Zhang et al., "Targeting the melanocortin-1 receptor with $^{177}$Lu-labeled alpha-melanocyte stimulating hormone derivatives: increased tumor uptake using an albumin binder," Journal of Nuclear Medicine, May 2018, 59 (Supplement 1): 1106.
AI, Hui-wang et al., "Exploration of new chromophore structures leads to the identification of improved blue fluorescent proteins", Biochemistry 2007, 46(20), 5904-5910.
Aimetti, Alex A. et al., "On-resin peptide macrocyclization using thiol-ene click chemistry", Chem. Commun., 2010, 46(23), 4061-4063.
Ala, Srinivasa, R. et al., "1,2,3-Triazole Rings as a Disulfide Bond Mimetic in Chimeric AGRP-Melanocortin Peptides Design, Synthesis, and Functional Characterization", ACS Chem. Neurosci., 2018, 9(5), 1001-1013.
Al-Obeidi, Fahad et al., "Potent and Prolonged Acting Cyclic Lactam Analogs of Alpha-Melanotropin—Design Based Jn Molecular Dynamics", J. Med. Chem., 1989, 32(12), 2555-2561.
Angell, Yu et al., "Ring closure to beta-tum mimics via copper-catalyzed azide/alkyne cycloadditions", J. Org. Chem., 2005, 70(23), 9595-9598.
Assem, N. et al., "Acetone-Linked Peptides: A Convergent Approach for Peptide Macrocyclization and Labeling", Angew. Chem. Int. Ed., 2015, 54(30), 8665-8668.
Beierle, John M. et al., "Conformationally Homogeneous Heterocyclic Pseudotetrapeptides as Three-Dimensional Scaffolds for Rational Drug Design: Receptor-Selective Somatostatin Analogues", Angew. Chem. Int., Edit 2009, 48(26), 4725-4729.
Benson, James R. et al., "Ortho-Phthalaldehyde—Fluorogenic Detection of Primary Amines in Picomole Range—Comparison with Fluorescamine and Ninhydrin", Proc. Natl. Acad. Sci. USA, 1975, 72(2), 619-622.

Blackwell, Helen E. et al., "Highly efficient synthesis of covalently cross-linked peptide helices by ring-closing metathesis", Angew. Chem. Int. Ed., 1998, 37(23), 3281-3284.
Bock, Jonathan E et al., "Getting in Shape: Controlling Peptide Bioactivity and Bioavailability Using Conformational Constraints", ACS Chem. Biol. 2013, 8(3): 488-499.
Brown, Stephen P. et al., "Peptide/Protein Stapling and Unstapling: Introduction of s-Tetrazine, Photochemical Release, and Regeneration of the Peptide/Protein", J. Am. Chem. Soc., 2015, 137(12), 4034-4037.
Brunel, Florence M. et al., "Synthesis of constrained helical peptides by thioether ligation: application to analogs of gp41", Chem. Commun., 2005(20), 2552-2554.
Bushnell, David A., et al., "Structural basis of transcription: alpha-Amanitin-RNA polymerase II cocrystal at 2.8 A resolution", Proc. Nall. Acad. Sci., USA, 2002, 99(3), 1218-1222.
Cardote, Teresa A.F. et al., "Cyclic and Macrocyclic Peptides as Chemical Tools To Recognise Protein Surfaces and Probe Protein-Protein Interactions", ChemMedChem, 2016, 11(8), 787-794.
Chen, Cheng et al., "Ruthenium-Based Catalytic Systems Incorporating a Labile Cyclooctadiene Ligand with N-Heterocyclic Carbene Precursors for the Atom-Economic Alcohol Amidation Using Amines", Molecules, 2018, 23, 10 pages.
Chen, Raymond F. et al., "Fluorescence Properties of Ortho-Phthalaldehyde Derivatives of Amino Acids", Biochim. Biophys. Acta, 1979, 576(2): 440-455.
Chung, Benjamin K.W., "Disulfide-bridged peptide macrobicycles from nature", Org. Biomol. Chem., 2015, 13(33), 8768-8779.
Cistrone, Philip A. et al., "Rigid Peptide Macrocycles from On-Resin Glaser Stapling", ChemBioChem, 2018, 19 (10), 1031-1035.
Craik, David J. et al., "The cystine knot motif in toxins and implications for drug design", Toxicon, 2001, 39(1), 43-60.
Craik, David J. et al., "The Future of Peptide-based Drugs", Chem. Biol. Drug. Des., 2013, 81(1), 136-147.
Cromm, Philipp M. et al., "Orthogonal ring-closing alkyne and olefin metathesis for the synthesis of small GTPase-targeting bicyclic peptides", Nature Communications, 2016, 7:11300, 7 pages.
Cupido, T. et al., "The synthesis of naturally occurring peptides and their analogs", Curr. Opin. Drug. Discov. Dev., 2007, 10(6), 768-783.
Dorr, Robert T. et al., "Evaluation of Melanotan-11, a superpotent cyclic melanotropic peptide in a pilot phase-I clinical study", Life Sci., 1996, 58(20), 1777-1784.
Ericson, Mark D. et al., "A Macrocyclic Agouti-Related Protein/[Nle(4), DPhe(7)]alpha-Melanocyte Stimulating Hormone Chimeric Scaffold Produces Subnanomolar Melanocortin Receptor Ligands", J. Med. Chem., 2017, 60(2), 805-813.
Fass, D. et al., "Chemistry and Enzymology of Disulfide Cross-Linking in Proteins", Chem. Rev. 2018, 118 (3), 1169-1198.
Faulstich, H. et al., "Ether Derivatives of Alpha-Amanitin—Introduction of Spacer Moieties, Lipophilic Residues and Radioactive Labels", Biochemistry, 1981, 20(22), 6498-6504.
Frost, John R., et al., "Oxadiazole grafts in peptide macrocycles", Nat. Chem., 2016, 8(12), 1105-1111.
Gavenonis, Jason et al., "Comprehensive analysis of loops at protein-protein interfaces for macrocycle design", Nat. Chem. Biol., 2014, 10(9), 716-722.
Goto, Yuki et al., "Reprogramming the translation initiation for the synthesis of physiologically stable cyclic peptides", ACS Chem. Biol., 2008, 3(2), 120-129.
Hallen, Heather E. et al., "Gene family encoding the major toxins of lethal Amanita mushrooms", Proc. Natl. Acad. Sci., USA, 2007, 104(48), 19097-19101.
Heim, Roger et al., "Engineering green fluorescent protein for improved brightness, longer wavelengths and fluorescence resonance energy transfer", Curr. Biol., 1996, 6(2), 178-182.
Heinis, Christian et al., "Phage-encoded combinatorial chemical libraries based on bicyclic peptides", Nat. Chem. Biol., 2009, 5(7). 502-507.
Hilinski, G. et al., "Stitched alpha-Helical Peptides via Bis Ring-Closing Metathesis", J Am Chem Soc 2014, 136(35): 12314-12322.

(56) References Cited

OTHER PUBLICATIONS

Hill, Timothy A. et al., "Constraining Cyclic Peptides To Mimic Protein Structure Motifs", Angew. Chem. Int. Ed., 2014, 53(48), 13020-13041.

Hirst, Barry H. et al., "Cyclic Hexa- and Pentapeptide Somatostatin Analogues with Reduced Gastric Inhibitory Activity", Peptide, 1984, 5, 857-860.

Holder, Jerry Ryan et al., "Melanocortin ligands: 30 years of structure-activity relationship (SAR) studies", Med. Res. Rev., 2004, 24(3), 325-356.

Ingale, Sampat et al., "On Resin Side-Chain Cyclization of Complex Peptides Using CuAAC", Org. Lett., 2011, 13 (11), 2822-2825.

Ishida, Y. et al., "New Detection and Separation Method for Amino-Acids by High-Performance Liquid-Chromatography", J. Chromatogr., 1981, 204(JAN), 143-148.

Kalhor-Monfared, S. et al., "Rapid biocompatible macrocyclization of peptides with decafluoro-diphenylsulfone" Chem. Sci., 2016, 7(6), 3785-3790.

Kostansek, Edward C. et al., "Conformation of Mushroom Toxin Beta-Amanitin in Crystalline State." Biochemistry 1978, 17(18), 3790-3795.

Kostansek, Edward C. et al., "The Crystal-Structure of Mushroom Toxin Beta-Amanitin", J. Am. Chem. Soc., 1977, 99(4), 1273-1274.

Lau, Yu Heng et al., "Peptide stapling techniques based on different macrocyclisation chemistries", Chem. Soc. Rev., 2015, 44(1), 91-102.

Lee, Kang S., et al., "Fluorometric Amino-Acid-Analysis with Ortho-Phthalaldehyde", Int. J. Biochem., 1978, 9(7), 457-467.

Li, Huiyuan et al., "Click Chemistry in Peptide-Based Drug Design". Molecules, 2013, 18(8), 9797-9817.

Ma, Bing et al., "Total Synthesis of the Antimitotic Bicyclic Peptide Celogentin", J. Am. Chem. Soc., 2010, 132(3), 1159-1171.

Maly, Dustin J. eta l., "A mechanism-based cross-linker for the identification of kinase-substrate pairs", J. Am. Chem. Soc., 2004, 126(30), 9160-9161.

Martinez-Ceron, Maria C. et al., "Latest Advances in OBOC Peptide Libraries. Improvements in Screening Strategies and Enlarging the Family From Linear to Cyclic Libraries", Curr. Pharm. Biotechnol., 2016, 17(5), 449-457.

Matinkhoo, Kaveh et al., "Synthesis of the Death—Cap Mushroom Toxin alpha-Amanitin", J. Am. Chem. Soc., 2018, 140(21), 6513-6517.

Matteucci, G. et al., "Active site labeling of erythrocyte transglutaminase by o-phthalaldehyde", Biol. Chem., 1998, 379(7), 921-924.

May, Jonathan P. et al., "Tryptathionine bridges in peptide synthesis", PeptideScience, 2007, 88(5), 714-724.

Mayorov, Alexander V. et al., "Effects of macrocycle size and rigidity on melanocortin receptor-1 and -5 selectivity in cyclic lactam alpha-melanocyte-stimulating hormone analogs", Chem. Biol. Drug Des., 2006, 67(5), 329-335.

Meldal, Morten et al., "Cu-catalyzed azide-alkyne cycloaddition", Chem. Rev., 2008, 108(8), 2952-3015.

Mendive-Tapia, Lorena et al., "New peptide architectures through C—H activation stapling between tryptophan-phenylalanine/tyrosine residues", Nature Communications, 2015, 6:7160, 9 pages.

Morin Eau, Gilles et al., "Reaction of o-phthalaldehyde with Amino Acids and Glutathione-Application to High Performance Liquid-Chromatography Determination", J. Chromatogr., 1989, 467(1), 209-216.

Ng, S. et al., "Bacteriophages and Viruses as a Support for Organic Synthesis and Combinatorial Chemistry", ACS Chem. Biol., 2012, 7(1), 123-138.

Oneil, K.D. et al., "Identification of Novel Peptide Antagonists for GPIIB/IIIA from a Conformationally Constrained Phage Peptide Library", Proteins, 1992, 14(4), 509-515.

Portoghese, Philip S., et al., "Affinity labels as tools for the identification of opioid receptor recognition sites", II Farmaco, 2001, 56(3), 191-196.

Puri, Rajinder N. et al., "Inactivation of Yeast Hexokinase by Ortho-Phthalaldehyde—Evidence for the Presence of a Cysteine and a Lysine at or Near the Active-Site", Biochim. Biophys. Acta 1988, 957(1), 34-46.

Puri, Rajinder N. et al., "Reaction of Low-Molecular Weight Aminothiols with o-Phthalaldehyde", Anal Biochem 1988, 173(1): 26-32.

Qin, Tian, et al., "A general alkyl-alkyl cross-coupling enabled by redox-active esters and alkylzinc reagents", Science 2016, 352(6287), 801-805.

Raposinho, Paula D. et al., "Melanocortin-1 Receptor-Targeting With Radiolabeled Cyclic alpha-Melanocyte-Stimulating Hormone Analogs for Melanoma Imaging", Biopolymers., 2010, 94(6), 820-829.

Rhodes, Curran A. et al., "Bicyclic Peptides as Next-Generation Therapeutics", Chem. Eur. J., 2017, 23(52), 12690-12703.

Rodriguez, Luis M.D. et al., "Chemical Synthesis of Bioactive Naturally Derived Cyclic Peptides Containing Ene-Like Rigidifying Motifs", Chem. Eur. J., 2018, 24(68), 17869-17880.

Ross, Avena C. et al., "Synthesis of the Lanlibiotic Lactocin S Using Peptide Cyclizations on Solid Phase", J, Am. Chem. Soc., 2010, 132(2), 462-463.

Roth, Marc, "Fluorescence Reaction for Amino Acids", Anal. Chem., 1971, 43(7), 880-882.

Silvestri, Anthony P. et al., "Adapting the Glaser Reaction for Bioconjugation: Robust Access to Structurally Simple, Rigid Linkers", Angew. Chem. Int. Ed., 2017, 56(35), 10438-10442.

Simons, S. Stoney et al., "Fluorescent Chemoaffinity Labeling—Potential Application of a New Affinity Labeling Technique to Glucocorticoid Receptors", Biochemistry, 1979, 18(22), 4915-4922.

Sousbie, Marc et al., "Structural Optimization and Characterization of Potent Analgesic Macrocyclic Analogues of Neurotensin (8-13)", J. Med. Chem., 2018, 61(16): 7103-7115.

Spokoyny, Alexander M. et al., "A Perfluoroaryl-Cysteine SNAr Chemistry Approach to Unprotected Peptide Stapling", J. Am. Chem. Soc., 2013, 135(16), 5946-5949.

Statsu K, Alexander V. et al., "Tuning a Three-Component Reaction for Trapping Kinase Substrate Complexes", J. Am. Chem. Soc., 2008, 130(51), 17568-17574.

Stobaugh, J.F. et al., "Aspects of the stability of isoindoles derives from the reaction of o-phthalaldehyde-ethanethiol, with primary amino compounds", Journal of Pharmaceutical & Biomedical Analysis, 1986, 4(3), 341-351.

Stobaugh, J.F. et al., "Autoxidation of 1-(tert-butylthio)-2-(N-propyl)isoindole", J. Org. Chem., 1984, 49(22), 1306-4309.

Subach, Oksana M. et al., "Conversion of Red Fluorescent Protein into a Bright Blue Probe", Chem. Biol. 2008, 15(10), 1116-1124.

Tian, Yuan et al., "Stapling of unprotected helical peptides via photoinduced intramolecular thiol-yne hydrothiolation", Chem. Sci., 2016, 7(5), 3325-3330.

Todorovic et al., "Fluorescent Isoinodole Crosslink (FliCk) Chemistry: A Rapid, User-friendly Stapling Reaction," Angewandte Chemie, available online Jul. 18, 2019, 58(40): 14120-14124. (Year: 2019).

Tonelli, Alan E. et al., "Structure of Alpha-Amanitin in Dimethylsulfoxide Solution", Biopolymers, 1978, 17(8), 1973-1986.

Veber, Daniel F. et al., "A Potent Cyclic Hexapeptide Analog of Somatostatin", Nature, 1981, 292(5818), 55-58.

Veber, Daniel F. et al., "Conformationally Restricted Bicyclic Analogs of Somatostatin", Proc. Natl. Acad. Sci., USA 1978, 75(6): 2636-2640.

Wang, Conan K. et al., "Designing macrocyclic disulfide-rich peptides for biotechnological applications", Nat. Chem. Biol., 2018, 14(5): 417-427.

Wang, Y.X. et al., "A Thiol-Ene Coupling Approach to Native Peptide Stapling and Macrocyclization", Angew. Chem. Int. Edit., 2015, 54(37), 10931-10934.

Wessells, Hunter et al., "Synthetic melanotropic peptide initiates erections in men with psychogenic erectile dysfunction: Double-blind, placebo controlled crossover study", J. Urol., 1998, 160(2), 389-393.

(56) References Cited

OTHER PUBLICATIONS

Wieland, Theodor et al., "Amatoxins, Phallotoxins, Phallolysin, and Antamanide—Biologically Active Components of Poisonous Amanita Mushrooms", CRC Critical Reviews in Biochemistry, 1978, 5(3), 185-260.

Wieland, Theodor et al., "Unexpected Similarity of the Structures of the Weakly Toxic Amanitin (S)-Sulfoxide and the Highly Toxic (R)-Sulfoxide and Sulfone as Revealed by Proton Nuclear Magnetic-Resonance and X-Ray Analysis", Biochemistry, 1983, 22(5), 1264-1271.

Willey, Joanne M. et al., "Lanlibiotics: Peptides of diverse structure and function", Annu. Rev. Microbiol., 2007, 61, 177-501.

Wojcik, Paulina et al., "Peptide-based inhibitors of protein-protein interactions", Bioorg. Med. Chem. Lett., 2016, 26(3), 707-713.

Yan, C.C. et al., "Fluorometric-Determination of Monobromobimane and o-Phthalaldehyde Adducts of Gamma-Glutaminylcysteine and Glutathione—Application to Assay Gamma—Glutaminylcysteinyl Synthetase-Activity and Glutathione Concentration in Liver", J. Chromatogr. B-Biomed. Appl., 1995, 672(2), 217-224.

Yang, Ying-kui et al., Molecular basis for the interaction of Nle(4),D-Phe(7) melanocyte stimulating hormone with the human melanocortin-1 receptor (melanocyte alpha-MSH receptor), J. Biol. Chem. 1997, 272(37), 23000-23010.

Zhang, C. et al., "Melanoma Imaging Using 18F-Labeled alpha-Melanocyte-Stimulating Hormone Derivatives with Positron Emission Tomography", Mol. Pharm., 2018, 15(6), 2116-2122.

Zhang, Chengcheng et al., "Molecular Imaging and Radionuclide Therapy of Melanoma Targeting the Melanocortin 1 Receptor", Mol, Imaging, 2017, 16, 15 pages.

Zhang, Chi et al., "Arylation Chemistry for Bioconjugation", Angewandte Chemie (International ed in English), 2019, 58, 4810-4839.

Zhao, Bingchaun et al., "Constructing thioether-tethered cyclic peptides via on-resin intra-molecular thiol-ene reaction", J. Pept. Sci., 2016, 22(8), 540-544.

Cai, M. et al., "Systematic Backbone Conformational Constraints on a Cyclic Melanotropin Ligand Leads to Highly Selective Ligands for Multiple Melanocortin Receptors", J Med Chem, 2015, 58, 6359-6367.

Extended European Search Report for Application No. 19900988.7, dated Oct. 31, 2022, 7 pages.

Guo, H. et al., "Effects of the amino acid linkers on the melanoma-targeting and pharmacokinetic properties of 111In-labeled lactam bridge-cyclized alpha-MSH peptides" J Nucl Med, 2011, vol. 52, pp. 608-616.

Lee, L.H. et al., "Converting polar cyclic peptides into membrane permeable molecules using N-methylation", Peptide Science, 2018, 110, e24063, https://doi.org/10.1002/pep2.24063, 10 pages.

Lepage, M., et al., "Toward 18 F-Labeled Theranostics: A Single Agent that Can Be Labeled with 18F, 64Cu, or 177Lu," Chembiochem, 2020, vol. 21, No. 7, pp. 943-947.

* cited by examiner

3-FOPA  4-FOPA  3-NOPA  4-NOPA  4-BrOPA amanitin a: R = NH₂, b = OH    FIICk-amanitin-1
FIICk-amanitin-2

SEQUENCE LISTING

```
<160> NUMBER OF SEQ ID NOS: 10

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide- Formula I
<220> FEATURE:
<221> NAME/KEY: MOD_RES
<222> LOCATION: (1)..(1)
<223> OTHER INFORMATION: L or D amino acid
<220> FEATURE:
<221> NAME/KEY: MOD_RES
<222> LOCATION: (2)..(2)
<223> OTHER INFORMATION: L or D amino acid
<220> FEATURE:
<221> NAME/KEY: MOD_RES
<222> LOCATION: (3)..(3)
<223> OTHER INFORMATION: L or D amino acid
<220> FEATURE:
<221> NAME/KEY: MOD_RES
<222> LOCATION: (4)..(4)
<223> OTHER INFORMATION: L or D amino acid
<220> FEATURE:
<221> NAME/KEY: MOD_RES
<222> LOCATION: (5)..(5)
<223> OTHER INFORMATION: L or D amino acid

<400> SEQUENCE: 1
```

```
His Phe Arg Trp Cys
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic Peptide- Formula IIa
<220> FEATURE:
<221> NAME/KEY: MOD_RES
<222> LOCATION: (1)..(1)
<223> OTHER INFORMATION: L or D amino acid
<220> FEATURE:
<221> NAME/KEY: MOD_RES
<222> LOCATION: (2)..(2)
<223> OTHER INFORMATION: L or D amino acid
<220> FEATURE:
<221> NAME/KEY: MOD_RES
<222> LOCATION: (3)..(3)
<223> OTHER INFORMATION: L or D amino acid
<220> FEATURE:
<221> NAME/KEY: MOD_RES
<222> LOCATION: (4)..(4)
<223> OTHER INFORMATION: L or D amino acid

<400> SEQUENCE: 2

His Phe Arg Trp
1

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide- Formula III
<220> FEATURE:
<221> NAME/KEY: MOD_RES
<222> LOCATION: (2)..(2)
<223> OTHER INFORMATION: D-amino acid

<400> SEQUENCE: 3

His Phe Arg Trp
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (2)..(2)
<223> OTHER INFORMATION: D-amino acid

<400> SEQUENCE: 4

His Phe Arg Trp Cys
1               5

<210> SEQ ID NO 5
<211> LENGTH: 5
<212> TYPE: PRT
<213> ORGANISM: Artificial Sequence
<220> FEATURE:
<223> OTHER INFORMATION: Synthetic Peptide- Formula IV
<220> FEATURE:
<221> NAME/KEY: Cys
<222> LOCATION: (5)..(5)
<223> OTHER INFORMATION: Cys with a cyclic modification
```

```
<400> SEQUENCE: 5

His Phe Arg Trp Cys
1               5

<210> SEQ ID NO 6
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: "Ile" is dihydroxyisoleucine (DhIle)
<220> FEATURE:
<221> NAME/KEY: MOD_RES
<222> LOCATION: (1)..(1)
<223> OTHER INFORMATION: Modified with Bis-O-TBS
<220> FEATURE:
<221> NAME/KEY: MOD_RES
<222> LOCATION: (2)..(2)
<223> OTHER INFORMATION: "Xaa" is diaminoproprionic acid (Dap)
<220> FEATURE:
<221> NAME/KEY: MOD_RES
<222> LOCATION: (2)..(2)
<223> OTHER INFORMATION: Modified with Boc
<220> FEATURE:
<221> NAME/KEY: MOD_RES
<222> LOCATION: (6)..(6)
<223> OTHER INFORMATION: Modified with Trt
<220> FEATURE:
<221> NAME/KEY: MOD_RES
<222> LOCATION: (7)..(7)
<223> OTHER INFORMATION: Modified with Trt
<220> FEATURE:
<221> NAME/KEY: MOD_RES
<222> LOCATION: (8)..(8)
<223> OTHER INFORMATION: "Pro" is hydroxyproline (Hyp)
<220> FEATURE:
<221> NAME/KEY: MOD_RES
<222> LOCATION: (8)..(8)
<223> OTHER INFORMATION: Modified with OtBu

<400> SEQUENCE: 6

Ile Xaa Gly Ile Gly Cys Asn Pro
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: "Xaa" is diaminoproprionic acid (Dap)
<220> FEATURE:
<221> NAME/KEY: MOD_RES
<222> LOCATION: (1)..(1)
<223> OTHER INFORMATION: Modified with Boc
<220> FEATURE:
<221> NAME/KEY: MOD_RES
<222> LOCATION: (5)..(5)
<223> OTHER INFORMATION: Modified with Trt
<220> FEATURE:
<221> NAME/KEY: MOD_RES
<222> LOCATION: (6)..(6)
<223> OTHER INFORMATION: Modified with Trt
<220> FEATURE:
<221> NAME/KEY: MOD_RES
<222> LOCATION: (7)..(7)
<223> OTHER INFORMATION: "Pro" is hydroxyproline (Hyp)
<220> FEATURE:
<221> NAME/KEY: MOD_RES
```

```
<222> LOCATION: (7)..(7)
<223> OTHER INFORMATION: Modified with OtBu

<400> SEQUENCE: 7

Xaa Gly Ile Gly Cys Asn Pro
1               5

<210> SEQ ID NO 8
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: "Ile" is dihydroxyisoleucine (DhIle)
<220> FEATURE:
<221> NAME/KEY: MOD_RES
<222> LOCATION: (2)..(2)
<223> OTHER INFORMATION: "Xaa" is diaminoproprionic acid (Dap)
<220> FEATURE:
<221> NAME/KEY: MOD_RES
<222> LOCATION: (8)..(8)
<223> OTHER INFORMATION: "Pro" is hydroxyproline (Hyp)

<400> SEQUENCE: 8

Ile Xaa Gly Ile Gly Cys Asn Pro
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: "Ile" is dihydroxyisoleucine (DhIle)
<220> FEATURE:
<221> NAME/KEY: MOD_RES
<222> LOCATION: (2)..(2)
<223> OTHER INFORMATION: "Xaa" is diaminoproprionic acid (Dap)
<220> FEATURE:
<221> NAME/KEY: MOD_RES
<222> LOCATION: (2)..(2)
<223> OTHER INFORMATION: Chemically modified - Condensation with
      o-phthalaldehyde
<220> FEATURE:
<221> NAME/KEY: MOD_RES
<222> LOCATION: (6)..(6)
<223> OTHER INFORMATION: Chemically modified - Condensation with
      o-phthalaldehyde
<220> FEATURE:
<221> NAME/KEY: MOD_RES
<222> LOCATION: (8)..(8)
<223> OTHER INFORMATION: "Pro" is hydroxyproline (Hyp)

<400> SEQUENCE: 9

Ile Xaa Gly Ile Gly Cys Asn Pro
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: "Ile" is dihydroxyisoleucine (DhIle)
```

```
<220> FEATURE:
<221> NAME/KEY: MOD_RES
<222> LOCATION: (2)..(2)
<223> OTHER INFORMATION: Chemically modified - Condensation with
      o-phthalaldehyde
<220> FEATURE:
<221> NAME/KEY: MOD_RES
<222> LOCATION: (6)..(6)
<223> OTHER INFORMATION: "Xaa" is diaminoproprionic acid (Dap)
<220> FEATURE:
<221> NAME/KEY: MOD_RES
<222> LOCATION: (6)..(6)
<223> OTHER INFORMATION: Chemically modified - Condensation with
      o-phthalaldehyde
<220> FEATURE:
<221> NAME/KEY: MOD_RES
<222> LOCATION: (8)..(8)
<223> OTHER INFORMATION: "Pro" is hydroxyproline (Hyp)

<400> SEQUENCE: 10

Ile Cys Gly Ile Gly Xaa Asn Pro
1               5
```

CYCLIC PEPTIDE ANALOGS OF MELANOCORTIN AND AMANITIN AND METHODS OF MAKING SUCH

CROSS-REFERENCE TO RELATED APPLICATIONS

This application is a continuation of U.S. patent application Ser. No. 16/804,465, filed on Feb. 28, 2020, which claims priority to U.S. Provisional Patent Application No. 62/812,410 filed Mar. 1, 2019, each disclosure is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: A9TH_014_02US_SeqList_ST25.txt, date recorded: Aug. 9, 2023, file size 5,256 bytes).

TECHNICAL FIELD

This invention relates to methods of cyclization of biologicals, such as peptides (e.g. melanocortins and amatoxins), using a cross-linking approach. In particular, the invention relates to linear and cyclic derivatives of the naturally occurring peptide alpha-melanocyte stimulating hormone (alpha-MSH), which has application in therapy, imaging, and targeted therapy, and to bicyclic peptide analogs of amanitin with florescent properties.

BACKGROUND

The pursuit of secondary structure stabilization is an ubiquitous goal in peptide chemistry and of central importance to the utilization of peptides as medicinal probes and high affinity ligands[1]. To this end, Nature typically employs oxidative disulfide formation from two cysteine thiols[2]. Disulfide crosslinks are also exploited in the development of synthetic peptides as drugs and imaging agents[3]. Since disulfide linkages are labile under reducing conditions, Nature uses redox-inert crosslinks in natural products, most notably, thioethers, as seen in the lanthionine antibiotics[4], tryptathionine linkages as seen amatoxins and phallotoxins[5], and heteroaryl crosslinks between tryptophan and histidine as seen in celogentin[6], in addition to several that have been recently reviewed[7]. These chemical crosslinks are critical to the biological activity of these molecules, whose syntheses are of enduring interest[8]. In considering the potency of these peptide natural products, the development of facile, synthetic crosslinking methodologies continues to be an active field of study. Such strategies offer the potential for truncating longer natural peptide sequences, thus facilitating scalable synthesis and improving pharmacokinetics[9]. More importantly, crosslinks rigidify the scaffold by reducing flexibility to favor a limited envelope of secondary structures. When applied properly, conformational restriction may dramatically improve both affinity and specificity[9e, 10].

Towards these ends, many well-known reactions within the synthetic repertoire have been repurposed for novelty in peptide crosslinking as reviewed extensively[11]; key examples include stapling by olefin cross-metathesis[12], Glaser alkyne synthesis[13], Cu-catalyzed triazole formation[14], oxadiazole formation[15], a host of thioether-forming reactions[16], and novel alkylation[17] and arylation reactions[18], all of which augment the many standard reactions made possible by commercially available homo- and heterobifunctional crosslinking reagents. Whereas rapidity, chemoselectivity, and high-yielding outcomes represent critical necessities of a given crosslinking method, they are not sufficient to guarantee high affinity (specific examples of crosslinked peptides with comparatively elevated $K_d$s include analogs of octreotatel[14c] and α-MSH[19]). Moreover, few crosslinking methods afford the added advantage of an emergent fluorescent signature as a direct consequence of crosslinking to provide spectroscopic evidence of successful reaction. Therefore, new crosslinking methods are needed that not only increase stability of the secondary peptide structure but also introduce useful features, such as fluorescence, to the structure.

DESCRIPTION

Inspired by certain indole-derived crosslinks found in highly strained peptide natural products, we sought such a facile and highly chemoselective crosslinking reaction for generating bioactive mono- and bicyclic peptides that would be accompanied by the prospect of emergent fluorescence. An outstanding candidate reaction that simultaneously meets these multiple criteria may be the condensation of an amine, a thiol, and ortho-phthalaldehyde (OPA) that may result in a highly fluorescent isoindole. Further advantages may include the use of mildly basic, transition metal-free, aqueous conditions that may be compatible with most biological molecules as well as high atom-economy.

Isoindole synthesis is known in other contexts; most commonly it is used analytically to quantify peptides of unknown extinction coefficients whereby free amines (N-terminus, lysines) are converted to highly fluorescent isoindoles in the presence of excess thiol[20]. Ortho-phthaladehyde has also been used in mechanistic enzymology as an active-site titrant[21] and as an affinity label for studying steroid and opioid receptors[22] and kinases[23]. Yet apart from a few isolated reports on isoindole crosslinking of glutathione for the sake of analytical/mechanistic applications[24], the use of OPA to drive crosslinking between a side-chain amine and a cysteine with concomitant fluorescent isoindole formation (FIG. 1) to form mono- and bicyclic peptides remains undocumented in the vast literature of peptide crosslinking reactions.

While it would be obvious to those trained in the art of peptide synthesis and stapling to consider this application in the context of any number of peptide lengths (e.g. peptides of 4-20 amino acids in length) to test this application, we sought a clinically relevant peptide known to require a β-turn motif for high-affinity target binding. Alpha-melanocyte stimulating hormone (α-MSH) provided an ideal test case: its interactions with melanocortin receptors require a specific β-turn motif that has been extensively exploited in the context of linear and monocyclic peptides ranging from 4-10 amino acids[25]. High-affinity α-MSH derivatives are of considerable interest for imaging[26] and treating melanoma[27], based on targeting the melanocortin-1 receptor (MC1-R) that is specifically expressed in the majority of melanomas.

Hence, we began our investigation by preparing four linear heptapeptide precursors containing a single cysteine to address different lengths of the amine. All were cyclized in a single, rapid, high-yielding step to provide new MSH analogs with fluorescent isoindole crosslinks that show high affinity denoted by low (single-digit) nanomolar dissociation constants. Because isoindole condensation remains an unexplored area of study, we synthesized five additional OPAs to access a portfolio of corresponding isoindoles with altered photophysical properties and increased photostability, all of which are installed late stage within 15 min. Finally, we applied the same strategy for intra-annular crosslinking of an octapeptide macrocycle to create a bicycle; in a preliminary test, we prepared an analog of α-amanitin wherein the isoindole replaces the characteristic tryptathionine crosslink. Surprisingly, this new bicyclic product showed detectable cytotoxicity that is further understood with corroborating molecular modelling. In light of the ease, rapidity, chemoselectivity, and robustness of this reaction, we have named this approach, "FlICk-ing"—fluorescent iso-indole crosslinking. Based on these promising results, we posit that this work will have broad applications to peptide and protein chemistry (vide infra).

Furthermore, the resulting crosslinked peptide may be endowed with both rigidity and the added value of fluorescence in the context of a highly biologically active and medicinally relevant peptide sequence. Additionally beneficial may be the fact that the fluorophore is incorporated into the main structure of the peptide, instead of appended onto one of the termini or onto a side chain. Thus implying that the structure of the peptide arrived at through discovery may be already the structure of a viable fluorescent probe. This obviates the need for post sequence discovery/optimization fluorescent derivatization, which can often negatively impact the binding affinity. Employing fluorescent isoindole crosslinking (FLIC) towards discovery and optimization may result in lead that require no further structural elaboration to synthesize probes.

SUMMARY

The invention described herein is based in part on the discovery of a protein/peptide crosslink, which introduces fluorescent properties, and which has been applied to synthesize analogues of melanocortin and amanitin as choice peptides to be explored in the context of isoindole peptides. Without limitation, it is expected that those trained in the art of peptide synthesis and stapling would appreciate the consequences of this invention such that other peptides of varied length can be similarly constrained by isoindole staples as featured herein.

In one embodiment the invention described herein provides a method of creating an intramolecular crosslinking within a peptide comprising: (a) Providing a peptide composition that further comprises at least one thiol group and at least one amine group and (b) reacting the peptide with a crosslinking agent of Formula VIII.

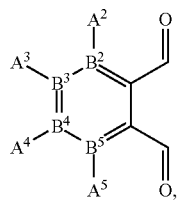
(Formula VIII)

Wherein:
$A^2$, $A^3$, $A^4$ and $A^5$ may be hydrogen, halogen, $NO_2$, CN, alkyne, azide, aryl, heteroaryl, COOH, $SO_3^-$, $CF_3$, RCO, CONHR, $NH_2$, NHR, $NR_2$, ether, thioether, hydroxyl, or boronate; wherein R may be an alkyl or alkenyl, optionally substituted; and $B^2$, $B^3$, $B^4$ and $B^5$ may be carbon or nitrogen.

In one embodiment the present invention comprises a linear analogue of alpha-MSH of Formula I $$R^1\text{-}R^2\text{—}R^*\text{—}X^1\text{—}X^2\text{—}X^3\text{—}X^4\text{—}R^3\text{-}R^4 \quad \text{(Formula I)};$$

wherein $R^1$ optionally may —H or —Ac;
$R^2$ may be -Nle-;
$X^1$ may be -His- or -D-His-;
$X^2$ may be -Phe- or -D-Phe-;
$X^3$ may be -Arg- or -D-Arg-;
$X^4$ may be -Trp- or -D-Trp-;
$R^3$ may be -Cys- or -D-Cys-;
$R^4$ optionally may be —H or —$NH_2$;
$R^*$ may be —NH—CH($R^\#NH_2$)—C(=O)—$NH_2$; and
wherein $R^\#$ may be a linear and optionally substituted alkyl.

In another embodiment the present invention comprises a linear analogue of alpha-MSH, wherein R* may be

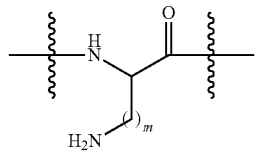 [SMILES: *NC(CN)C(*)=O]

with m=1-15.

In another embodiment the present invention comprises a cyclic analogue of alpha-MSH of Formula IIa

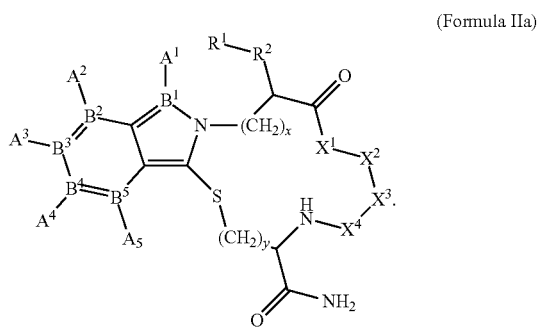
(Formula IIa)

In another embodiment the present invention comprises a cyclic analogue of alpha-MSH of Formula IIb

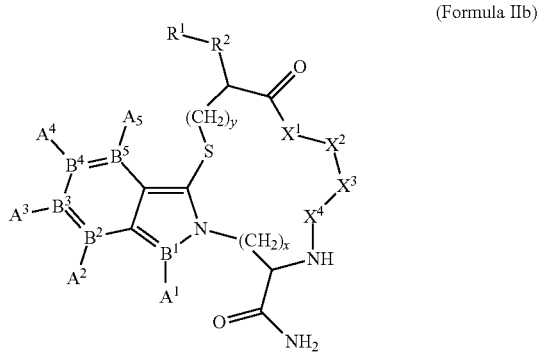
(Formula IIb)

Wherein R¹ optionally may be Ac— or H—;

R² may be -Nle-;

X¹ may be -His- or -D-His-;

X² may be -Phe- or -D-Phe-;

X³ may be -Arg- or -D-Arg-;

X⁴ may be -Trp- or -D-Trp-;

$A^{1-5}$ may be hydrogen, halogen, $NO_2$, CN, alkyne, azide, aryl, heteroaryl, $SO_3^-$, $CF_3$, RCO, COOH, CONHR, $NH_2$, NHR, $NR_2$, ether, thioether, hydroxyl, or boronate; wherein R may be an alkyl or alkenyl, optionally substituted;

$B^{1-5}$ may be carbon or nitrogen; and x and y independently may be a natural number between 1-15.

In another embodiment the present invention comprises a cyclic analogue of alpha-MSH of Formula IIc:

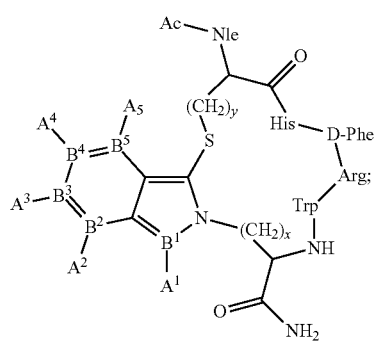

(Formula IIc)

wherein variables may be defined as above.

In a further embodiment the present invention comprises a cyclic analogue of alpha-MSH of Formula III

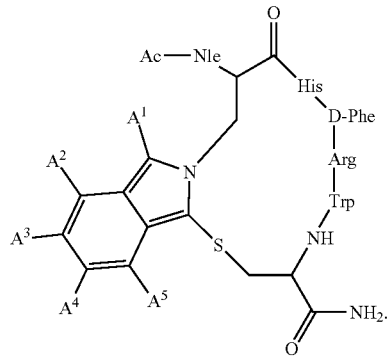

(Formula III)

In one embodiment the present invention comprises the following cyclic analogues of alpha-MSH (Formula IV a-d):

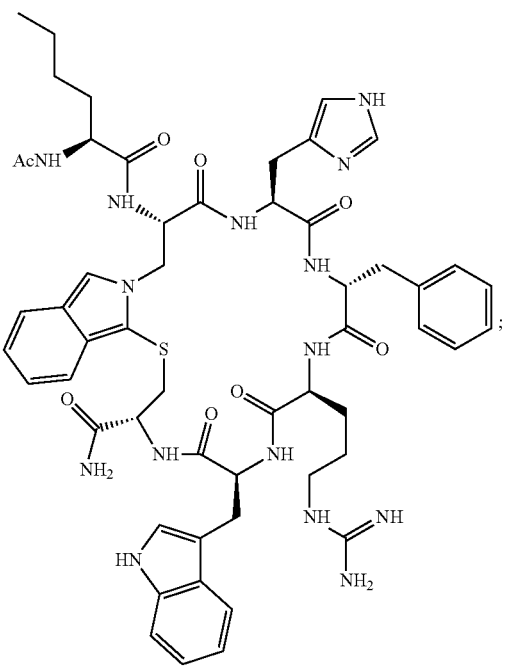

(Formula IVa)

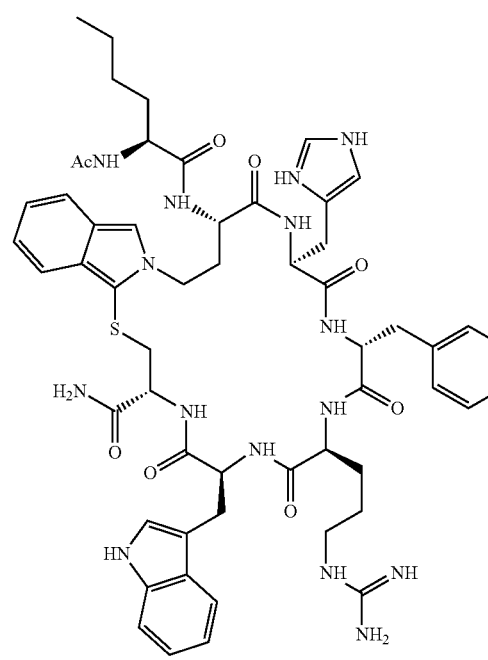

(Formula IVb)

-continued (Formula IVc)

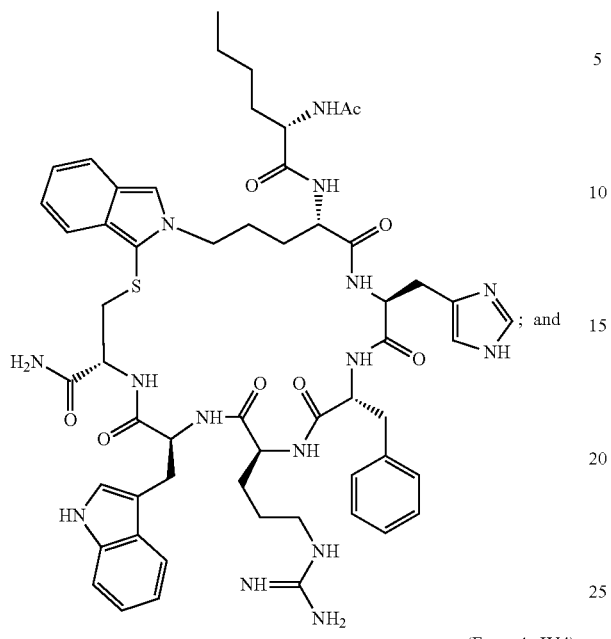

and (Formula IVd)

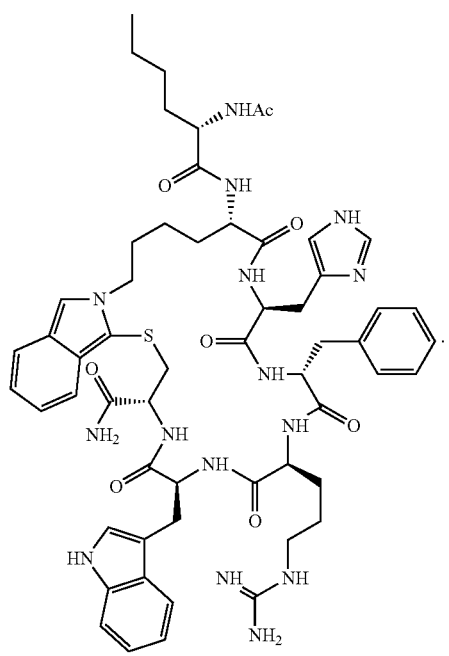

In a further embodiment the present invention comprises a pharmaceutical formulation of one or more compounds of Formula I-IV.

In a further embodiment the present invention comprises a cosmetic formulation of one or more compounds of Formula I-IV. Wherein the cosmetic formulation may further comprise a cosmetically-acceptable carrier or diluent.

In one embodiment the present invention comprises an amatoxin of Formula V:

(Formula V)

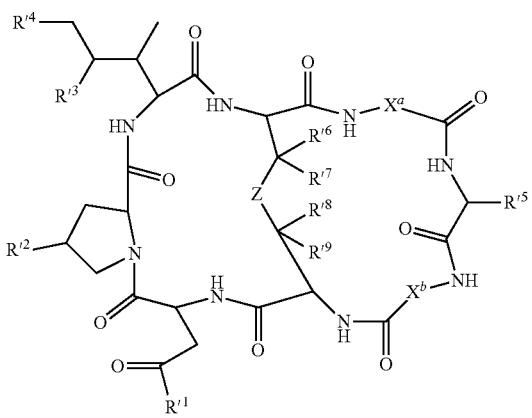

wherein $R'^1$ may be $NH_2$, OH, NHR', NHOR', or NHNHR';

$R'^2$ may be H, OH, OR', =O, $NH_2$, SH, NHR', $N_3$, $NH(C=NH_2^+)NH_2$ i.e. guanidinium, or CN;

$R'^3$ may be H, F, Cl, $NH_2$, $N_3$, =O, SH, NHR', OR', SR', or OH;

$R'^4$ may be H, F, Cl, $NH_2$, $N_3$, =O, SH, NHR', OR', SR', or OH;

$R'^5$ may be H, linear or cyclic alkyl or alkenyl, optionally further substituted and/or comprising heteroatoms;

$R'^6$, $R'^7$, $R'^8$, and $R'^9$ independently may be H, D, or alkyl that optionally further may be substituted and/or comprises heteroatoms;

$X^a$ and $X^b$ independently may be $(CH_2)_n$ with n=0-5, NH, or NR';

Z may be an isoindole;

R' may be wherein R' may be H, a linear or cyclic $C_{1-20}$ alkyl chain that may be optionally substituted, an aryl or a heterocycle that may be optionally substituted, a tertiary amide, or a linker group suitable for biomolecule conjugation.

Examples of said isoindoles for Z may comprise

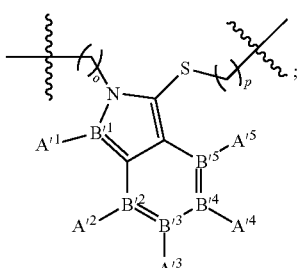

wherein $A'^{1-5}$ may be hydrogen, halogen, $NO_2$, CN, alkyne, azide, aryl, heteroaryl, $SO_3^-$, $CF_3$, RCO, COOH, CONHR, $NH_2$, NHR, $NR_2$, ether, thioether, hydroxyl, or boronate; wherein R may be an alkyl or alkenyl, optionally substituted;

$B'^{1-5}$ may be carbon or nitrogen; and o and p independently may be 0, 1, 2, 3, or 4.

In a further embodiment the present invention comprises an amatoxin of Formula IV, wherein Z may be

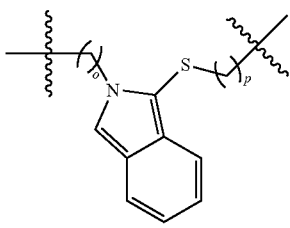

with o and p independently 0, 1, 2, 3, or 4.

In another embodiment the present invention comprises an amatoxin of Formula VI:

(Formula VI)

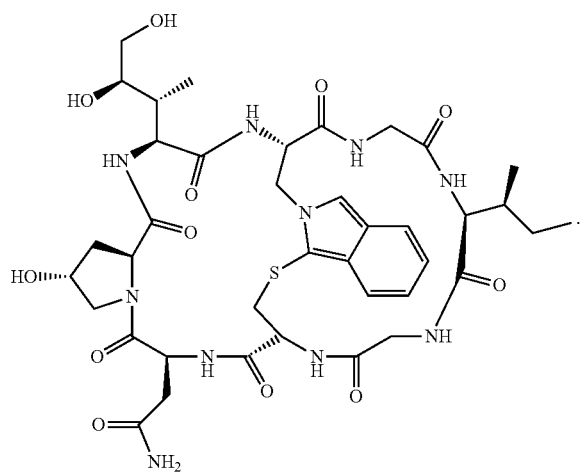

Wherein said amatoxin of Formula VI may be FlICk-amanitin-1.

In another embodiment the present invention comprises an amatoxin of Formula VII:

(Formula VII)

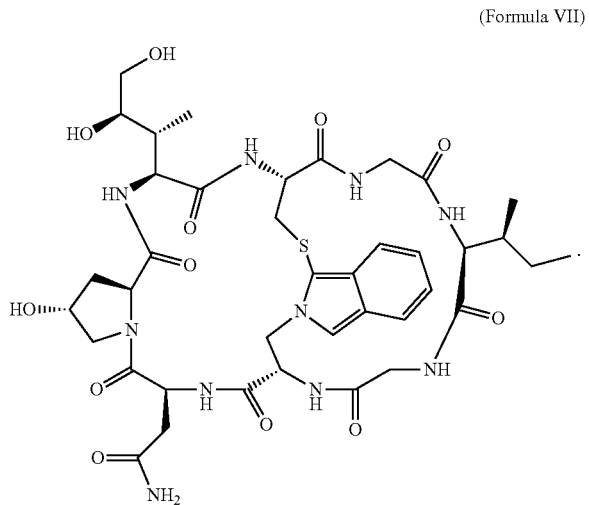 [SMILES: CC[C@H](C)[C@@H]1NC(=O)CNC(=O)[C@@H]2CSc3c4ccccc4cn3C[C@H](NC(=O)CNC1=O)C(=O)N[C@@H](CC(N)=O)C(=O)N1C[C@H](O)C[C@H]1C(=O)N[C@@H]([C@@H](C)[C@@H](O)CO)C(=O)N2]

Wherein said amatoxin of Formula VII may be FlICk-amanitin-2.

In a further embodiment, the present invention comprises a pharmaceutical composition of any one or more compounds of Formula V-VII.

In one embodiment the present invention comprises the use of one or more compounds of Formula I-IV to increase alpha-MSH activity in a subject in need thereof.

In another embodiment the present invention comprises the use of one or more compounds of Formula I-IV for the manufacture of a medicament having melanotropic activity.

In a further embodiment the present invention comprises the use of one or more compounds of Formula I-IV as an inhibitor binding to melanocortin receptor 1 (MCR1).

In a further embodiment the present invention comprises the diagnostic use of one or more compounds of Formula I-IV. For example, as medical imaging agents.

In a further embodiment the present invention comprises the use of one or more compounds of Formula I-IV for the diagnosis and/or treatment of neurodegenerative diseases. Wherein examples of neurodegenerative diseases may comprises multiple sclerosis (MS), amyotrophic lateral sclerosis (ALS), dementia, Alzheimer's disease, Parkinson's disease, and Huntington's disease.

In a further embodiment the present invention comprises the use of one or more compounds of Formula I-IV for the treatment of skin associated diseases. Wherein examples of skin associated diseases may comprise photosensitivity, photodermatoses, psoriasis, bullous disease, and Hailey-Hailey disease.

In a further embodiment, the present invention comprises a method of use of any one or more of the compounds of Formula V-VII for use in the treatment of cancer in a subject in need thereof.

In one embodiment the present invention provides a method of cyclizing a peptide by strategically crosslinking a thiol group with an amine group, said method comprising:

(i) preparing a linear peptide of Formula I;
(ii) crosslinking said linear peptide of Formula I with a cross-linking agents to give a cyclized peptide of Formula III; and
(iii) optionally isolation and/or further reacting said cyclized peptide formed in step (ii).

Wherein said cross-linking agent may be a substituted aromatic compound, a fluorescent compound, a dye, Wherein said cross-linking agent may be a compound of Formula VIII:

(Formula VIII)

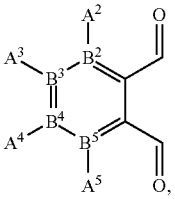

$A^{2-5}$ may be hydrogen, halogen, $NO_2$, CN, alkyne, azide, aryl, heteroaryl, $SO_3^-$, $CF_3$, RCO, COOH, CONHR, $NH_2$, NHR, $NR_2$, ether, thioether, hydroxyl, or boronate; wherein R may be an alkyl or alkenyl, optionally substituted; and $B^{2-5}$ may be carbon or nitrogen.

In one example said cross-linking agent may be specifically:

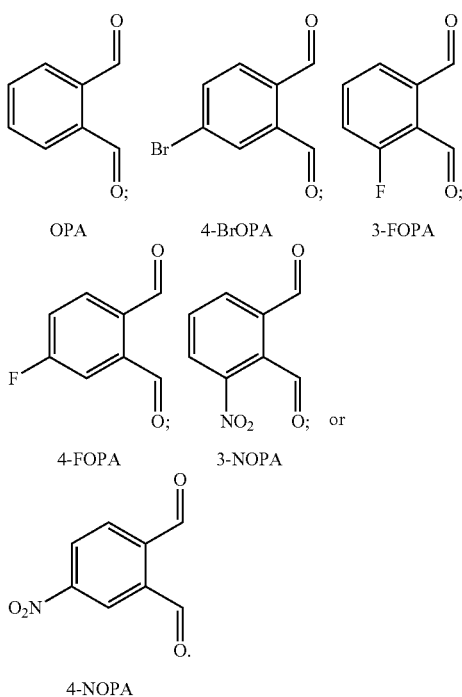

In one embodiment the present invention provides a method of cyclizing a peptide by strategically crosslinking a thiol group with an amine group, said method comprising:
  (i) making a solid phase compatible version of a heptapeptide;
  (ii) cleaving said heptapeptide from step (i) and coupling it with dihydroxyisoleucine;
  (iii) performing isoindole condensation to obtain a monocycle;
  (iv) macrolactamizing said octapeptide to provide said compound of Formula V; and
  (v) optionally deuterating said compound of Formula V.
  Wherein steps (iii) and (iv) may be conducted in reverse order.
  Wherein said heptapeptide may comprise diaminopropionic acids. For example, wherein said heptapeptide may be

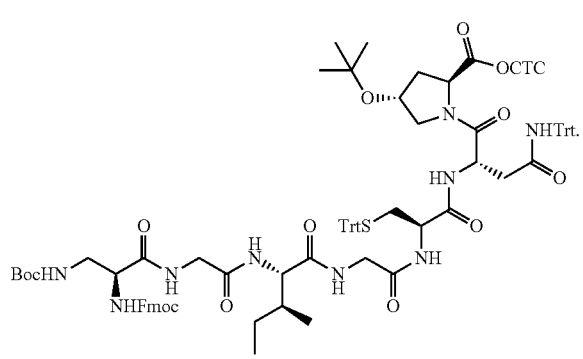

Wherein said deuterated version of said compound of Formula V from step (v) may be more metabolically stable.
Throughout this specification, unless the context requires otherwise, the words "comprise", "comprising" and the like, are to be construed in an inclusive sense as opposed to an exclusive sense, that is to say, in the sense of "including, but not limited to"

DESCRIPTION OF THE DRAWINGS

These and other features of the invention will become more apparent from the following description in which reference is made to the appended drawings.

DETAILED DESCRIPTION

Inspired by certain indole-derived crosslinks found in highly strained peptide natural products, we sought such a facile and highly chemoselective crosslinking reaction for generating bioactive mono- and bicyclic peptides that would be accompanied by the prospect of emergent fluorescence. An outstanding candidate reaction that simultaneously meets these multiple criteria may be the condensation of an amine, a thiol, and ortho-phthalaldehyde (OPA) that may result in a highly fluorescent isoindole. Further advantages may include the use of mildly basic, transition metal-free, aqueous conditions that may be compatible with most biological molecules as well as high atom-economy.

Figure 1:
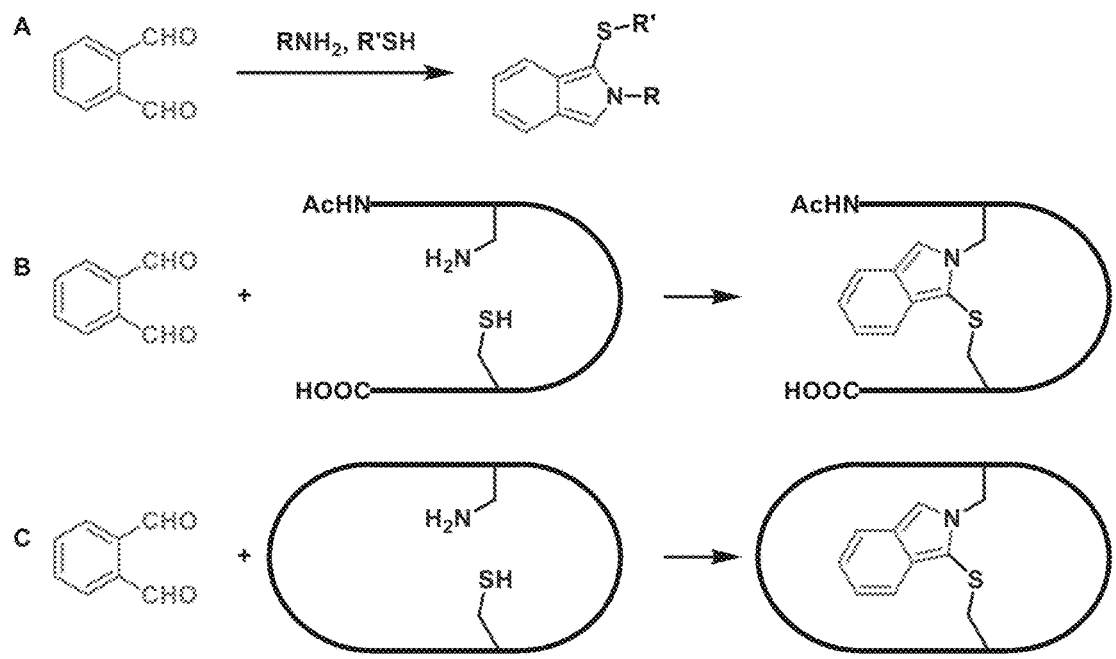
FIG. 1: A: standard termolecular condensation to give an isoindole to quantify the concentration of free amine in a peptide or biological sample; B: isoindole crosslinking on a linear peptide to give a macrocycle; C: isoindole crosslinking on a peptide macrocycle to give a bicyclic structure.

Isoindole synthesis is known in other contexts; most commonly it is used analytically to quantify peptides of unknown extinction coefficients whereby free amines (N-terminus, lysines) are converted to highly fluorescent isoindoles in the presence of excess thiol[20]. Ortho-phthalaldehyde has also been used in mechanistic enzymology as an active-site titrant[21] and as an affinity label for studying steroid and opioid receptors[22] and kinases[23]. Yet apart from a few isolated reports on isoindole crosslinking of glutathione for the sake of analytical/mechanistic applications[24], the use of OPA to drive crosslinking between a side-chain amine and a cysteine with concomitant fluorescent isoindole formation (FIG. 1) to form mono- and bicyclic peptides remains undocumented in the vast literature of peptide crosslinking reactions.

To test this application, we sought a clinically relevant peptide known to require a β-turn motif for high-affinity target binding. Alpha-melanocyte stimulating hormone (α-MSH) provided an ideal test case: its interactions with melanocortin receptors require a specific β-turn motif that has been extensively exploited in the context of linear and monocyclic peptides ranging from 4-10 amino acids[25]. High-affinity α-MSH derivatives are of considerable interest for imaging[26] and treating melanoma[27], based on targeting the melanocortin-1 receptor (MC1-R) that is specifically expressed in the majority of melanomas.

Hence, we began our investigation by preparing four linear heptapeptide precursors containing a single cysteine to address different lengths of the amine. All were cyclized in a single, rapid, high-yielding step to provide new MSH analogs with fluorescent isoindole crosslinks that show high affinity denoted by low (single-digit) nanomolar dissociation constants. Because isoindole condensation remains an unexplored area of study, we synthesized five additional OPAs to access a portfolio of corresponding isoindoles with altered photophysical properties and increased photostability, all of which are installed late stage within 15 min. Finally, we applied the same strategy for intra-annular crosslinking of an octapeptide macrocycle to create a bicycle; in a preliminary test, we prepared an analog of α-amanitin wherein the isoindole replaces the characteristic tryptathionine crosslink. Surprisingly, this new bicyclic product showed detectable cytotoxicity that is further understood with corroborating molecular modelling. In light of the ease, rapidity, chemoselectivity, and robustness of this reaction, we have named this approach, "FlICk-ing"—fluorescent iso-indole crosslinking. This work will have broad applications to peptide and protein chemistry (vide infra).

Furthermore, the resulting crosslinked peptide may be endowed with both rigidity and the added value of fluorescence in the context of a highly biologically active and medicinally relevant peptide sequence. Additionally beneficial may be the fact that the fluorophore is incorporated into the main structure of the peptide, instead of appended onto one of the termini or onto a side chain. Thus implying that the structure of the peptide arrived at through discovery may be already the structure of a viable fluorescent probe. This obviates the need for post sequence discovery/optimization fluorescent derivatization, which can often negatively impact the binding affinity. Employing fluorescent isoindole crosslinking (FLIC) towards discovery and optimization may result in lead that require no further structural elaboration to synthesize probes.

Materials and Methods

The procedures described herein are given for the purposes of example and illustration only and should not be considered to limit the spirit or scope of the invention.

General Peptide Synthesis Procedure

Unless otherwise indicated, all solvents and reagents were purchased from Sigma-Aldrich, Fischer Scientific, Alfa-Aesar and Cambridge Isotope Laboratories. Purchased products were used without further purification. Dry THF was obtained from distillation and stored with 4 Å molecular sieves, while other dry solvents such as DMF, DCM, EtOAc, and MeCN were dried over and stored with 4 Å molecular sieves at least one day prior to use. Columns used for purification were packed using SiliaFlash F60 (230-400 mesh silica gel from Silicycle, unless otherwise stated, in which case Merck Grade Silica purchased from Sigma Aldrich was used. Low resolution mass spectrometry data were acquired using a Waters ZQ GC-MS coupled to a Waters 2695 HPLC for the purposes of sample injection. High resolution mass spectrometry data were taken by Derick Smith on a Waters/Micromass LCT TOF Mass Spectrometer. $^1$H NMR, $^{13}$C NMR, $^{19}$F NMR, COSY, HSQC and HMBC spectroscopy data were collected on a 300 MHz Bruker Avance Spectrometer unless otherwise stated, in which case the data were collected on a 600 MHz Bruker Avance Spectrometer. All chemical shifts are reported in ppm (δ) scale, and are referenced to the solvent signal. HPLC purifications were performed using an Agilent 1100 Series paired with an Agilent Eclipse XDB-C18 column. Detection was through UV-Vis absorbance at 229 nm, 283 nm, 335 nm, or 450 nm depending on the product being eluted. Regular peptides were monitored at 283 nm due to tryptophan absorbance, isoindoles, 3-fluoro isoindoles and 4-fluoroisoindoles were measured at 335 nm, and 3 and 4 nitro isoindoles were detected at 450 nm.

O-Phthalaldehyde Derivatives

The methodology for the synthesis of all o-phthalaldehyde derivatives is largely the same as that for the sample 4-nitrophthalaldehyde synthesis below. Any details that differ are stated in the corresponding sections for the phthalaldehyde derivatives. Full spectra and characterization data can be found in appendix A.

4-Nitrophthalic Acid

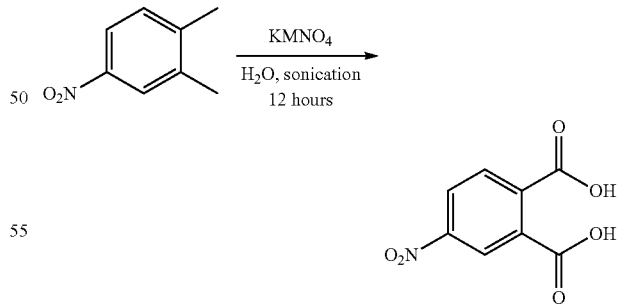

1,2-dimethyl-4-nitrobenzene (5.02 g, 33.18 mmol) was added to a deep purple solution of 150 mL of milliQ water and potassium permanganate (KMNO$_4$, 43.25 g, 288.27 mmol) and sonicated overnight. The reaction flask was then removed from the sonicator and quenched at 0° C. using KOH pellets and EtOH until the contents of the flask were dark brown. The resulting mixture was filtered to remove solid by-products and acidified to pH ~0 with concentrated HCl$_{(aq)}$. The acidified mixture was extracted into EtOAc (3×75 mL) and the organic layers were combined, dried with MgSO$_4$ and solvent was removed under reduced pressure. The resulting solid was used in the next step without purification. Yield: 3.03 g, 50%; $^1$H NMR (300 MHz, CD$_3$CN) δ 8.53 (d, J=2.3 Hz, 1H), 8.40 (dd, J=8.5, 2.3 Hz, 1H), 7.90 (d, J=8.5 Hz, 1H). $^{13}$C NMR (75 MHz, CD$_3$CN) δ 167.65, 166.48, 149.96, 139.06, 133.45, 131.08, 127.34, 125.12, 118.26. ESI-HRMS for C$_8$H$_5$NO$_6$: [M+Na$^+$]$^+$: calculated: 234.0009. found: 234.0015.

(4-nitro-1,2-phenylene)dimethanol

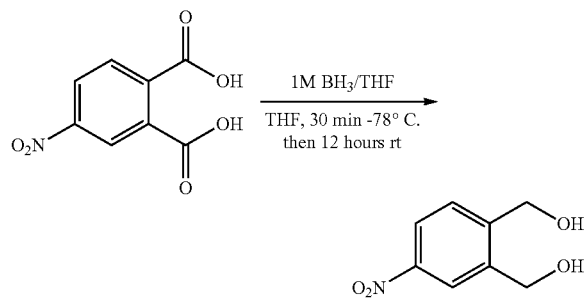

4-nitrophthalic acid (3.68 mmol, 772.8 mg) was added to a previously flame dried flask containing a stir bar and dry THF (1 mL). The mixture was stirred until no solids were observed. 1 M BH$_3$·THF solution (18.5 mmol, 18.5 mL) was then slowly added to the mixture at −78° C. The reaction was then stirred for 30 minutes at −78° C., then allowed to warm to room temperature and stir overnight. The mixture was quenched with THF/milliQ H$_2$O (20 mL, 1:1 v/v). An additional 100 mL milliQ H$_2$O was added to the resultant mixture which was then extracted into EtOAc (3×70 mL), dried with MgSO$_4$, filtered and had solvent removed under reduced pressure.

The resulting pale yellow solid was loaded onto a silica gel column with 98 DCM:2EtOH, and eluted with 96 DCM:4 EtOH. Pure fractions were collected and solvent was removed under reduced pressure to leave a pure white powdery solid. Yield: 0.49 g, 73.4%. $^1$H NMR (300 MHz, CD$_3$CN) δ 8.27 (d, J=2.4 Hz, 1H), 8.12 (dd, J=8.4, 2.4 Hz, 1H), 7.67 (d, J=8.4 Hz, 1H), 4.76-4.61 (m, 4H), 3.55-3.44 (m, 2H). $^{13}$C NMR (75 MHz, CD$_3$CN) δ 148.17, 147.59, 141.93, 128.56, 122.89, 122.28, 118.26, 61.50, 61.27. ESI-HRMS for C$_8$H$_9$NO$_4$: [M+Na$^+$]$^+$: calculated: 206.0424. found: 206.0429.

4-nitrophthalaldehyde

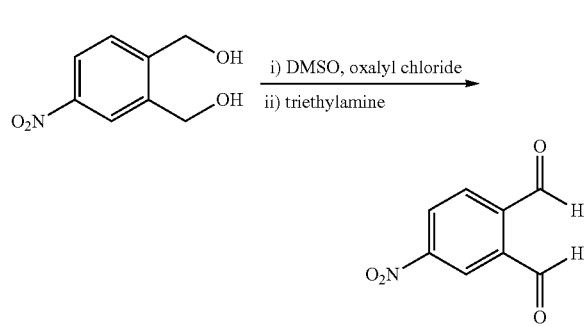

Dry dichloromethane (4 mL) was added to a previously flame dried round bottom flask. The mixture was cooled to −78° C., and oxalyl chloride (195 µl, 2.26 mmol) was added dropwise to the DCM with stirring. Next, dimethyl sulfoxide (250 µl, 3.50 mmol) was added dropwise to the mixture at −78° C., and the mixture was stirred for 15 minutes. The previously prepared (4-nitro-1,2-phenylene)dimethanol dissolved in a DCM/THF mixture (2 mL, 3 DCM:1 THF) was added dropwise and stirred at −78° C. for 2 hours. The flask containing was then rinsed with DCM/THF (2 mL, 3 DCM:1 THF). Neat trimethylamine (2.6 mL, 18.51 mmol) was added to the stirring mixture and then allowed to stir for 10 minutes at −78° C., then allowed to warm to room temperature and then stirred for 30 minutes. The reaction mixture was then quenched with methanol (15 mL), stirred for 10 minutes and solvent was evaporated under reduced pressure yielding a glassy solid. The resulting crude product was purified using a dry loaded column packed with Merck grade silica with 60 Hexanes: 39 EtOAc: 1 MeOH. Pure fractions were collected, pooled and the identity of the compound was confirmed by NMR spectroscopy. Yield: 0.11 g, 52.1%. $^1$H NMR (methyl hemiacetal in equilibrium with phthalaldehyde) (300 MHz, CD$_3$CN) δ 10.53 (s, 1H), 10.48 (s, 1H), 8.71 (d, J=2.3 Hz, 1H), 8.56 (dd, J=8.4, 2.3 Hz, 1H), 8.34-8.11 (m, 7H), 7.61 (m, 3H), 6.60-5.99 (m, 7H), 5.09 (m, 3H), 3.52-3.34 (m, 9H), 3.28 (s, 12H).

3-fluorophthalic acid

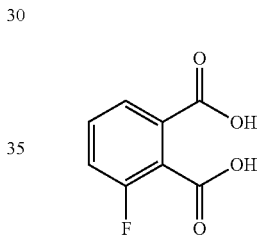

Yield: 1.83 g, 62.2%. $^1$H NMR (300 MHz, CD$_3$CN) δ 7.83-7.74 (m, 1H), 7.57 (td, J=8.1, 5.5 Hz, 1H), 7.48-7.39 (m, 1H). $^{13}$C NMR (75 MHz, CD$_3$CN) δ 166.15, 165.95, 161.31, 158.03, 132.47, 132.36, 130.71, 130.67, 126.97, 126.93, 124.66, 124.40, 121.30, 121.01, 118.26. $^{19}$F NMR (282 MHz, CD$_3$CN) δ −117.84 (dd, J=9.3, 5.6 Hz). ESI-HRMS for C$_8$H$_6$O$_4$F: [M+H$^+$]$^+$: calculated: 185.0245. found: 185.0250.

(3-fluoro-1,2-phenylene)dimethanol

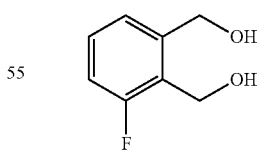

Yield: 0.39 g, 64.4%. $^1$H NMR (300 MHz, CD$_3$CN) δ 7.36-7.27 (m, 1H), 7.23 (d, J=7.1 Hz, 1H), 7.05 (m, 1H), 4.69 (t, J=5.8 Hz, 4H), 3.57 (t, J=5.8 Hz, 1H), 3.43 (t, J=5.8 Hz, 1H). $^{13}$C NMR (75 MHz, CD$_3$CN) δ 130.38, 130.25, 125.25, 125.22, 118.26, 115.54, 115.23, 62.89, 62.85, 54.85, 54.76. $^{19}$F NMR (282 MHz, CD$_3$CN) δ −121.07--121.30 (m). ESI-HRMS for C$_8$H$_9$O$_2$F: [M+Na$^+$]$^+$: calculated: 179.0497. found: 179.0484.

3-fluorophthalaldehyde

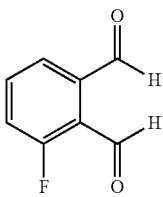

Yield: 0.14 g, 28.8% (Methyl acetal) ESI-HRMS for $C_{10}H_{11}O_3F$ (methyl acetal): $[M+Na^+]^+$: calculated: 221.0584. found: 221.0590. $^1H$ NMR (hemiacetal in equilibrium with phthalaldehyde) (300 MHz, $CD_3CN$) δ 10.46 (s, 1H), 10.31 (s, 1H), 7.79 (dd, J=8.0, 5.1 Hz, 1H), 7.71 (d, J=6.7 Hz, 1H), 7.55-7.40 (m, 20H), 7.28-7.06 (m, 40H), 6.63-5.95 (m, 40H), 4.87 (d, J=20.4 Hz, 20H), 3.76-3.58 (m, 30H), 3.35 (dd, J=14.0, 4.4 Hz, 14H).

4-bromophthalic acid

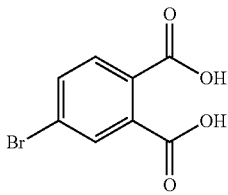 [SMILES: O=C(O)c1ccc(Br)cc1C(=O)O]

Yield: 4.43 g, 48.8%. $^1H$ NMR (300 MHz, $CD_3CN$) δ 7.88 (d, J=2.0 Hz, 1H), 7.76 (dd, J=8.3, 2.0 Hz, 1H), 7.68 (d, J=8.3 Hz, 1H). $^{13}C$ NMR (75 MHz, $CD_3CN$) δ 167.94, 167.59, 159.02, 135.16, 135.10, 132.56, 131.85, 131.38, 126.17, 118.26. ESI-HRMS for $C_8H_4O_4Br$: $[M-H^+]^-$: calculated: 242.9298. found: 242.9293.

(4-bromo-1,2-phenylene)dimethanol

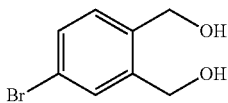

Yield: 0.433 g, 66.5%. $^1H$ NMR (300 MHz, $CD_3CN$) δ 7.56 (d, J=2.0 Hz, 1H), 7.43 (dd, J=8.1, 2.0 Hz, 1H), 7.30 (d, J=8.1 Hz, 1H), 4.58 (m, 4H), 3.43 (m, 2H). $^{13}C$ NMR (75 MHz, $CD_3CN$) δ 143.08, 139.57, 131.18, 130.97, 130.69, 121.56, 118.26, 62.06, 61.97. ESI-HRMS for $C_8H_9O_2Br$: $[M+Na^+]^+$: calculated: 238.9678. found: 238.9684.

4-bromophthalaldehyde

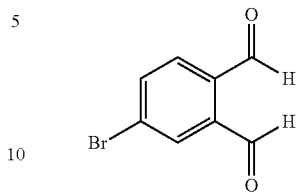

Yield: 0.257 g, 52.3%. $^1H$ NMR (300 MHz, $CD_3CN$) δ 10.43 (s, 1H), 10.41 (s, 1H), 8.10 (d, J=1.9 Hz, 1H), 8.01-7.97 (m, 1H), 7.88 (d, J=8.2 Hz, 1H). ESI-HRMS for $C_9H_9O_3Br$ (methyl hemiacetal): $[M+Na^+]^+$: calculated: 266.9627. found: 266.9633.

(3-nitro-1,2-phenylene)dimethanol

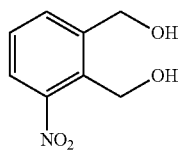 [SMILES: O=[N+]([O-])c1cccc(CO)c1CO]

Yield: 0.90 g, 69.5%. $^1H$ NMR (300 MHz, $CD_3CN$) δ 7.70 (m, 2H), 7.47 (t, J=7.9 Hz, 1H), 4.74 (m, 4H), 3.51 (m, 2H). ESI-HRMS for $C_8H_{10}O_4N$: $[M+Na^+]^+$: calculated: 184.0604. found: 184.0610.

3-nitrophthalaldehyde

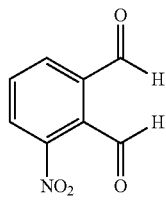

Yield: 0.1017 g, 29.4%. ESI-HRMS for $C_9H_9NO_5$ (methyl hemiacetal): $[M+Na^+]^+$: calculated: 234.0373. found: 234.0378. See table in results and discussion for NMR data.

General HPLC Method

Peptides were purified on an Agilent 1100 series HPLC outfitted with an Agilent Eclipse XDB-C18 column (5 μm internal diameter, 9.4×250 mm) using a linear gradient of solvent A (0.1% Formic Acid $H_2O$) and solvent B (0.1% Formic Acid MeCN at a flow rate of 2 mL/minute. The column had a void volume of approximately 12 mL (6 minutes.) The gradient went from 0 minutes (85% A, 15% B) to 18 minutes (65% A, 35% B) to 21 minutes (0% A, 100% B) to 26 minutes (0% A, 100% B) to 29 minutes (85% A, 15% B) to 37 minutes (85% A, 15% B.)

Model Isoindoles for Regioselectivity Studies and Photo-Physical Properties

Phthalaldehyde Peptide Quantification Assay[65]

A standard ONB (o-phthalaldehyde-N-acetyl cysteine-borate, 1:1:8) buffer was made using a phthalaldehyde of choice (0.05 M), N-acetyl cysteine (0.05 M), and sodium borate buffer (pH 9.5). This ONB buffer was distributed among 6 vials (3 mL ONB/vial). A standard hexylamine (HAM, 0.007M in MeCN/H$_2$O, 2:8 in 0.1% formic acid) solution was made and added, increasing incrementally to the 6 vials containing ONB buffer such that a standard curve was made (0-50 uL HAM). These vials were vortexed and then let sit for 30 minutes. Following this, the absorbance of each vial was read at the $\lambda_{max}$ of each respective isoindole. From these absorbance measurements, a standard curve was formed, from which the extinction coefficient of each phthalaldehyde was determined. In addition, this phthalaldehyde assay was used to determine the concentration of the linear peptides solutions synthesized earlier in the project.

Determining the $\lambda_{max}$ of Isoindoles

The $\lambda_{max}$ of each novel isoindole was determined using a wavelength scan on a sample of ONB buffer containing the phthalaldehyde of interest (1.5 mL) reacted with HAM (25 uL). The machine was blanked and a baseline was taken on two ONB samples without HAM added. The spectrometer was used in double beam mode, with one blank ONB sample as a reference.

N-acetyl-S-(2-hexyl-5-nitro-2H-isoindol-1-yl)-L-cysteine

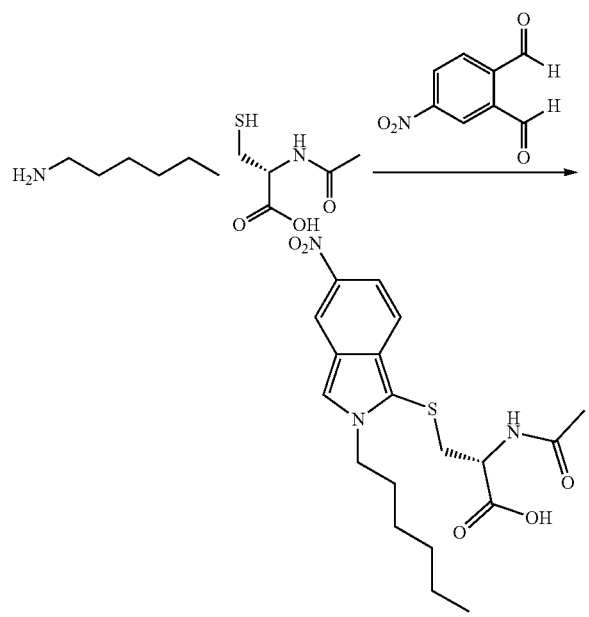

A solution of 4-nitrophthalaldehyde (0.05 M in DMF, 750 μL) was mixed with N-acetyl cysteine (NAc) (0.10 M in DMF, 750 μL) and borate buffer (6 mL, pH 9.5), followed by neat hexylamine (HAM) (25 μL). The mixture was vortexed until it turned a dark orange color. O-phosphoric acid was then added to the reaction mixture until it reached pH 2, upon which it turned a bright orange. The reaction mixture was then extracted into diethyl ether (3×5 mL) and solvent was removed under reduced pressure. The mixture was then column purified on Merck grade silica with 90 DCM:8 EtOH:2 AcOH. Fractions containing the product were collected and solvent was removed under reduced pressure.

General Procedure for Solid Phase Peptide Synthesis

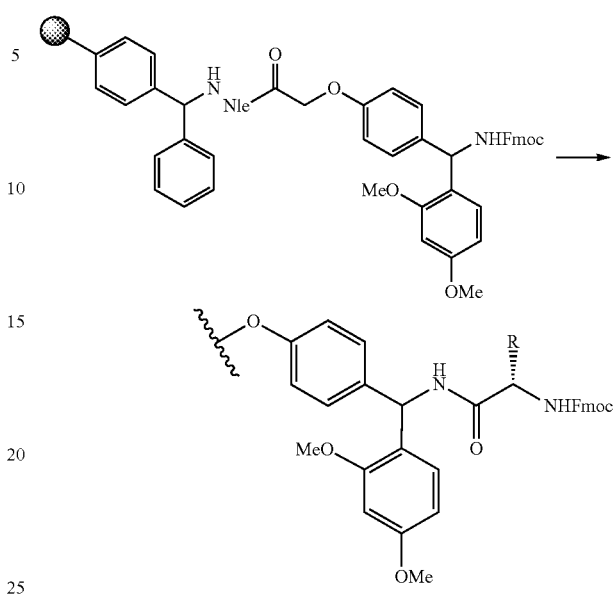

The dried resin contained in a ZEBA Desalt spin column was solvated in 5 mL DMF and shaken for at least 30 minutes. The solvent was drained and the resin was resuspended in 5 mL 2:8 Piperidine/DMF (0.5M Oxyma) and shaken for 5 minutes. The solvent was drained and the resin was resuspended in 5 mL 2:8 Piperidine/DMF (0.5M Oxyma) and shaken for a further 10 minutes. The solvent was drained and the resin was washed with seven 5 mL portions of DMF, with shaking and draining. The resin was then Kaiser tested and if a positive result (purple or brown) was observed, the beads were then resuspended in a 5 mL solution of DMF which already contained 4 equivalents each of Fmoc-Xaa, Oxyma and COMU and ~11 equivalents DIEA. The resin was then shaken for 1-3 hours at room temperature. The solvent was drained and the resin was washed with five 5 mL portions of DMF, with shaking and draining. The resin was then Kaiser tested and if a negative result (no change in colouration) was observed, the beads were then resuspended in a 5 mL solution of 1:2:2 Ac$_2$O/Collidine/EtOAc and shaken for 20 minutes at room temperature. If the result of the Kaiser test remained positive, another coupling with same Fmoc amino acid was performed. Once the capping was complete, The solvent was drained and the resin was washed with five 5 mL portions of DMF, with shaking and draining. The resin was then washed with DCM and left to dry under reduced pressure if couplings were complete for the day or resuspended in 2:8 Piperidine/DMF (0.5M Oxyma) for the next Fmoc deprotection.

General Procedure for Peptide Resin Cleavage

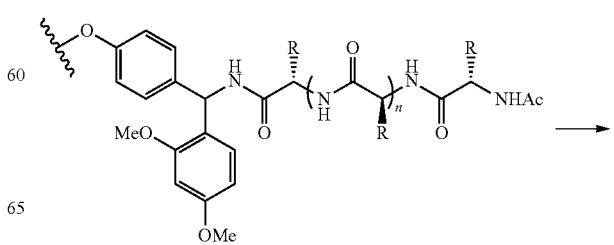

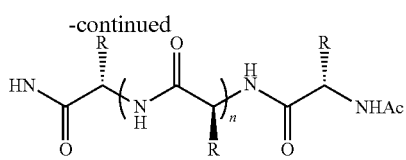

To the spin column containing the N-acetylated resin bound peptide was added 5 mL 95:2.5:2.5 v/v/v TFA/TIS/H$_2$O and the beads were shaken at room temperature for 2 hours. The filtrate was evaporated under reduced pressure to yield a brown or pinkish solid. The last traces of TFA were removed by two successive rounds of co-evaporation with DCM. The crude peptide was then triturated with three 10 mL portions of Et$_2$O and allowed to air dry overnight to yield an off-white powder. The crude material was purified on a reverse-phase SEP-PACK column (Waters, 3 cc.) Loaded with 0.1% Formic acid H$_2$O (10 mL,) eluted with successive 10 mL portions of 5:95 MeCN/H$_2$O (0.1% Formic acid,) 10:90 MeCN/H$_2$O (0.1% Formic acid,) 15:85 MeCN/H$_2$O (0.1% Formic acid,) 20:80 MeCN/H$_2$O (0.1% Formic acid,) and 40:60 MeCN/H$_2$O (0.1% Formic acid.) Fractions were checked for purity and presence of the product. The purest and most abundant in product fractions where pooled, frozen and lyophilized.

General Fluorescent Isoindole Crosslinking (FLIC) Procedure:

Loading of 2-CTC Resin with Fmoc-Hyp(OtBu)-OH

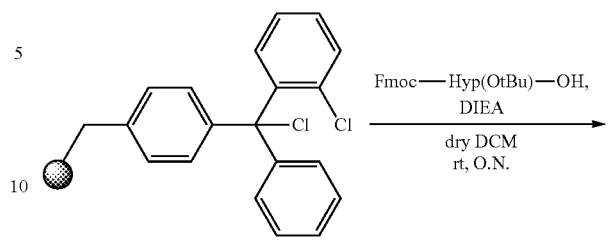

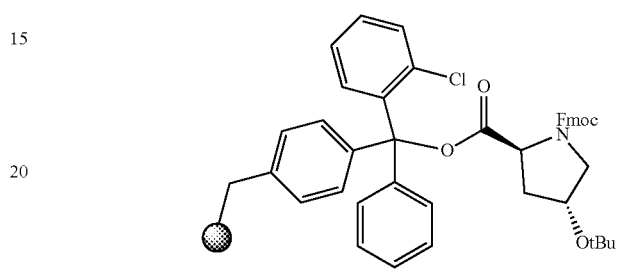

1 g (1.2 mmol) of 2-CTC resin was dried against P$_2$O$_5$ in a desiccator on the high vac line for 4 h. The resin was then

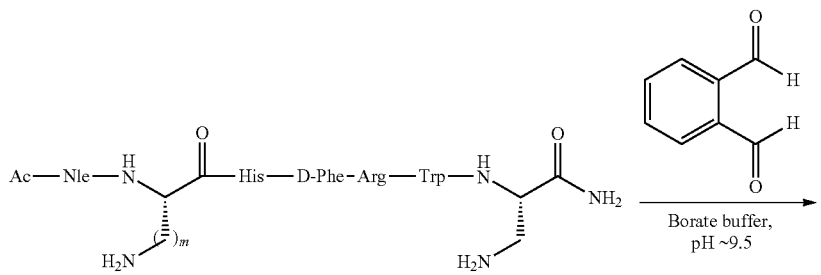

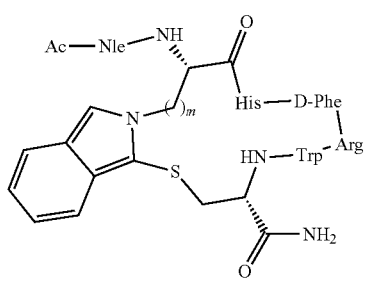

0.5 µmoles of lyophilized linear peptide in the bottom of a 15 mL Falcon Tube was dissolved in 50 µL of Sodium Borate buffer (pH-9.5) and 15 µL of 50 mM φ-phthalaldehyde (solution in EtOH) was added at room temperature. The tube was then vortexed at room temperature for 30 seconds. After the appearance of precipitate (5-30 minutes), 35 µL of DMF was added to the reaction mixture to achieve a clear solution. At this point, the entire reaction mixture was injected directly into the HPLC system for immediate purification. The product peak was manually collected, immediately frozen and lyophilized (product tube was wrapped in foil) to yield a white or coloured fluffy powder (28-77% yield).

transferred to a flame dried round bottom flask under argon and 0.982 g (2.4 mmol, 2 eq) of Fmoc-Hyp(OtBu)-OH was added the flask. The solids were dissolved/suspended in 7.5 mL dry DCM and the reaction mixture was stirred at room temperature. 1.045 mL DIEA (6 mmol, 5 eq) was added dropwise to the stirring solution and the reaction was allowed to proceed over night. 1 mL MeOH was then added and the reaction was stirred for 1 h. The resin was then transferred to a spin column and the resin was thoroughly washed with DCM and dried on vacuum. The solid phase synthesis proceed to the Heptapeptide detailed below as per the general solid phase peptide synthesis procedure outlined in this document.

Synthesis of H₂N-Dap(Boc)-Gly-Ile-Gly-Cys(Trt)-Asn(Trt)-Hyp(OtBu)-OH

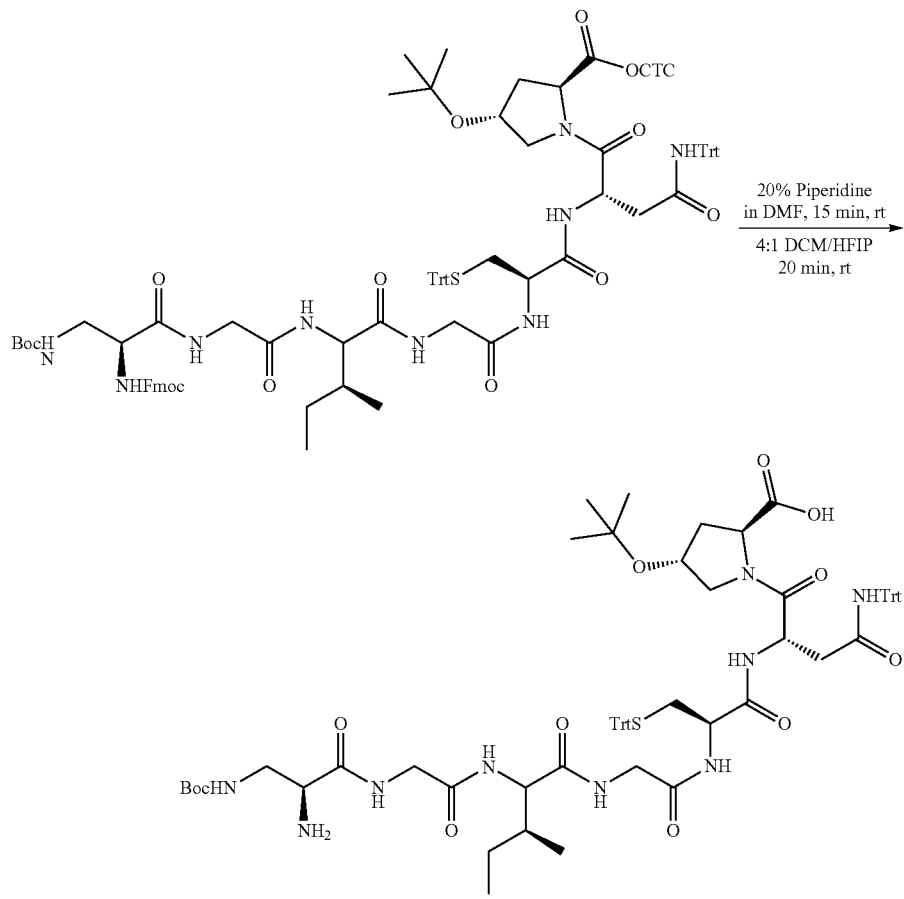

The Fmoc protected, resin bound heptapetide was synthesized as detailed above. 100 mg of the resin was then suspended in 5 mL 20% Piperidine in DMF (0.5M) Oxyma and shaken for 5 minutes at room temperature. The solution was drained from the spin column and then 5 mL of fresh 20% Piperidine in DMF (0.5M Oxyma) was added and the solution was shaken for a further 10 minutes at room temperature. The deprotection solution was then drained and the resin was resuspended in DMF, shaken and drained. This washing procedure was repeated a further 6 times. The resin was then washed with DCM and Kaiser tested. Upon confirmation of the presence of free amine, the resin was resuspended in 5 mL of a 4:1 v/v solution of DCM/HFIP and shaken at room temperature for 20 minutes. The solution was then drained into a round bottom flask and the resin was washed with DCM and these rinses were pooled with the original filtrate. The solution was then evaporated under reduced pressure to yield a pinkish beige solid which was used in the next step with no further purification. (42.3 mg, 32.5 μmol). HRMS (m/z) [M+H]⁺ calcd. for $C_{72}H_{88}N_9O_{12}S$, 1302.6273; found 1302.6376.

Synthesis of (2S,3R,4R)—Oγ,Oδ-bis-TBS-Nα-Fmoc-dihydroxyisoleucine-NHS

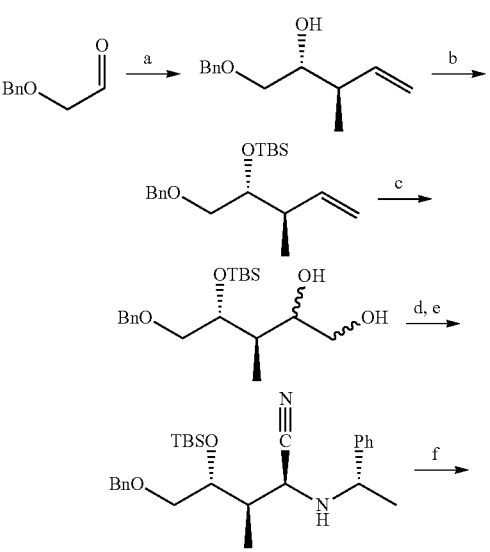

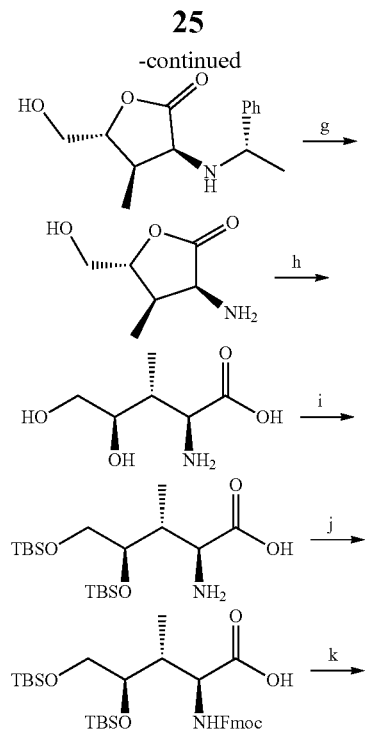

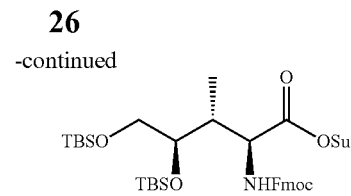

Reagents and conditions: a) E-Butene, dry tBuOK, BuLi, dry THF, −78° C. then (+)-(Ipc)$_2$BOMe then BF$_3$-Et$_2$O, then Benzyloxy-acetaldehyde −78° C., 4 h, then NaOH, H$_2$O$_2$, reflux, 1 h. 92% yield. b) TBDMSOTf, 2,6-Lutidine, DCM, 4° C. to rt, 6 h. 48% yield. c) OsO$_4$, NMO, Acetone/H$_2$O rt, O.N. 54% yield. d) NaIO$_4$, MeOH/H$_2$O, rt, 1 h. 73% yield. e) S-Phenylethylamine, KCN, MeOH/H$_2$O rt, 3 days. 39% yield. f) 6MHCl, reflux, 6 h. 66% yield. g) H$_2$, MeOH, rt O.N. h) LiOH, H$_2$O, rt, 4.5 h. i) TBDMSCl, Imidazole, dry DMA, rt O.N. j) Fmoc-Osu, Na$_2$CO$_3$, 1,4-dioxane/H$_2$O. 22% overall yield over 4 steps. k) DSC, Collidine, EtOAc/MeCN, 4° C. to rt, 6 hours. 70% yield.

All spectra matched a previous literature report[38].

Synthesis of H$_2$N-DhIle(Bis-O-TBS)-Dap(Boc)-Gly-Ile-Gly-Cys(Trt)-Asn(Trt)-Hyp(OtBu)-OH

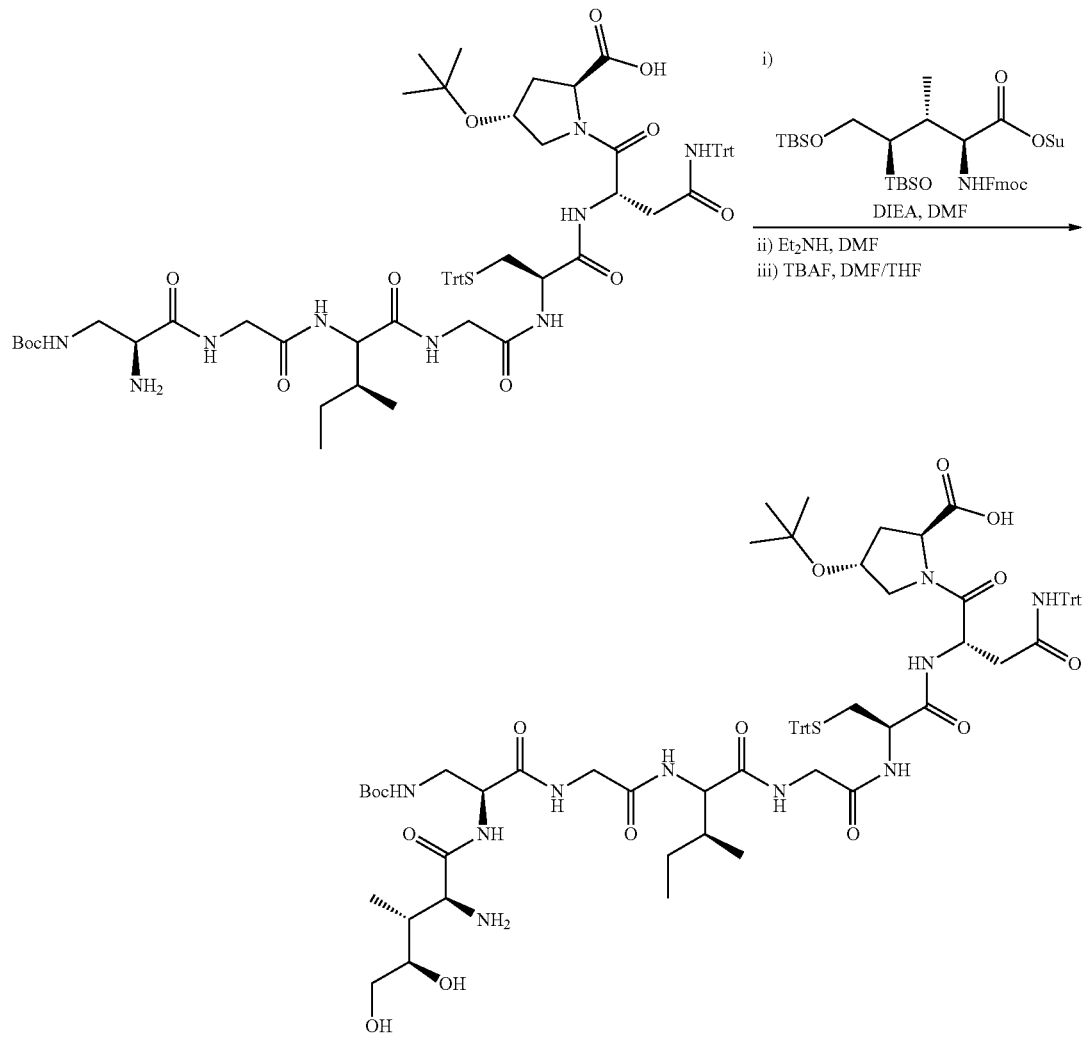

i) H₂N-Dap(Boc)-Gly-Ile-Gly-Cys(Trt)-Asn(Trt)-Hyp(OtBu)-OH (42.3 mg, 32.5 μmol) was dissolved in 87 μL DMF in 2 mL flat bottom vial and 14.1 μL DIEA (8.1 μmol, 2.5 eq) was to added to solution along with 34.8 mg (2S,3R,4R)—Oγ,Oδ-bis-TBS-Nα-Fmoc-dihydroxyisoleucine-NHS (48.8 μmol, 1.5 eq.) The mixture was stirred overnight at room temperature.

ii) Upon completion of the acylation, 20 μL Et₂NH was added to solution and the reaction was stirred for 2 h at room temperature. The volatiles were then evaporated and the crude was placed on the high vac line overnight.

iii) The resulting gel was dissolved in 600 μL DMF and 200 μL 1.0M TBAF in THF solution was added, the resulting solution was stirred at room temperature for 2 and a half hours. Upon completion of the deprotection (as assessed by LRMS-ESI) the reaction mixture was diluted with 10 mL 1:1 H₂O/MeCN (0.1% Formic Acid), shell frozen and lyophilized. The resulting gel was purified on Reverse-Phase SEP-PACK, using gradient elution from 7:3 H₂O/MeCN (0.1% Formic Acid) to 2:8 H₂O/MeCN (0.1% Formic Acid.) The fractions containing the product were pooled, frozen and lyophilized to yield a fluffy white powder. (22.4 mg, 15.5 μmol 48% yield over 3 steps.). HRMS (m/z) [M+H]⁺ calcd. for $C_{78}H_{99}N_{10}O_{15}S$, 1447.7012; found 1447.7018.

Macrolactamization and Global Deprotection of H₂N-DhIle(Bis-O-TBS)-Dap(Boc)-Gly-Ile-Gly-Cys(Trt)-Asn(Trt)-Hyp(OtBu)-OH

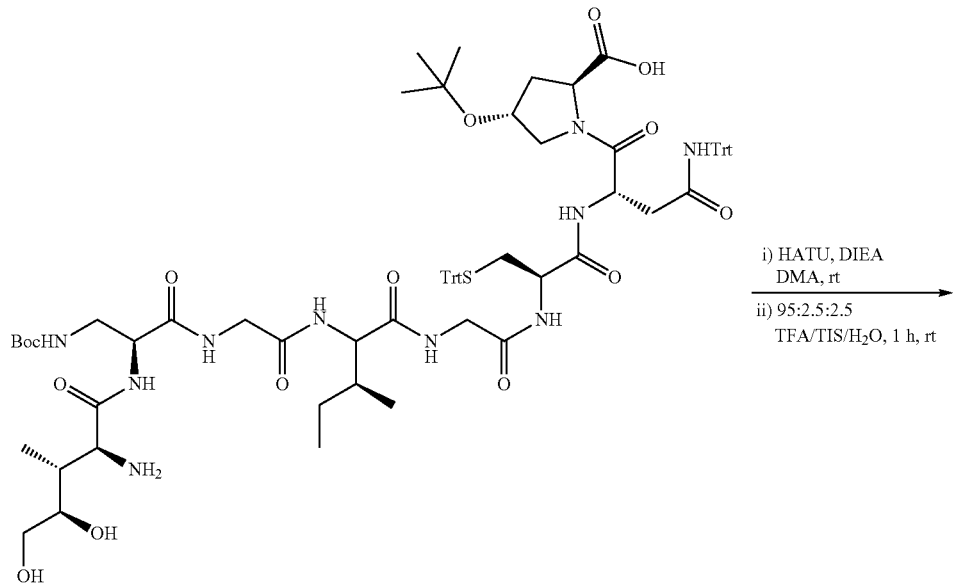

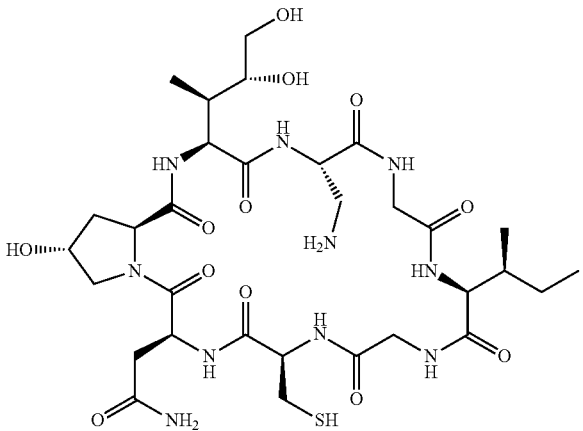

i) H$_2$N-DhIle(Bis-O-TBS)-Dap(Boc)-Gly-Ile-Gly-Cys(Trt)-Asn(Trt)-Hyp(OtBu)-OH (22.4 mg, 15.5 µmol) was dissolved in 4 mL DMA, 53 mg HATU (139 µmol, 9 eq) was added to the reaction mixture along with 26.9 µL DIEA (155 µmol 10 eq) and the solution was stirred at room temperature for 1 h. Upon completion of the reaction (as assessed by LRMS-ESI) the reaction mixture was diluted with 20 mL H$_2$O, shell frozen and lyophillized.

ii) Half of the resulting solid was dissolved in 1 mL 95:2.5:2.5 TFA/TIS/H$_2$O in a round bottom flask and stirred for 1 h at room temperature. The volatiles were evaporated under reduced pressure and the resulting solid was triturted with one cold 10 mL portion of Et$_2$O. The resulting solid was purified Reverse-Phase SEP-PACK, using gradient elution from 1:0 H$_2$O/MeCN (0.1% Formic Acid) to 7:3 H$_2$O/MeCN (0.1% Formic Acid.) The fractions containing the product were pooled, frozen and lyophilized to yield a fluffy white powder. (Quantitative yield over 2 steps, contaminated with HATU). HRMS (m/z) [M+H]$^+$ calcd. for C$_{31}$H$_{53}$N$_{10}$O$_{12}$S, 789.3565; found 789.3567.

Condensation of cyclo-[DhIle-Dap-Gly-Ile-Gly-Cys-Asn-Hyp] with o-phthalaldehyde

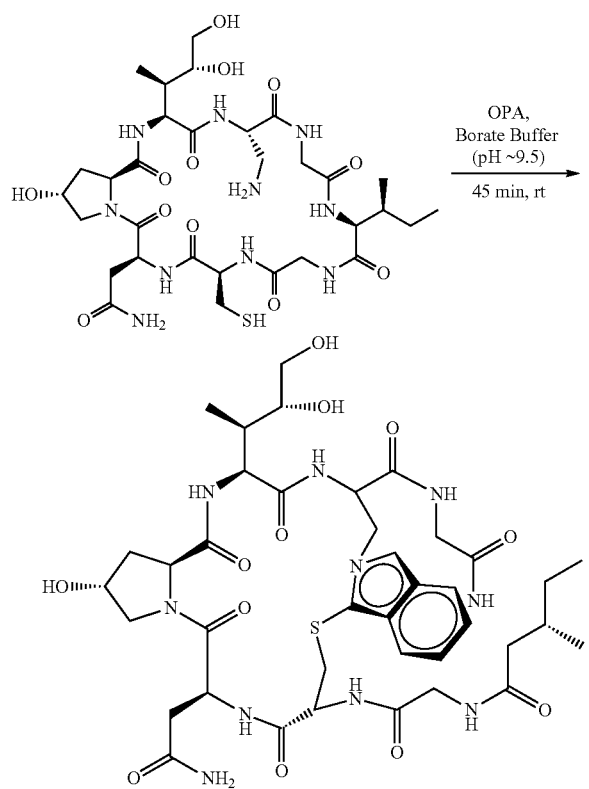

0.5 µmoles of lyophilized monocyclic peptide in the bottom of a 15 mL Falcon Tube was dissolved in 80 µL of 50 mM TCEP in Sodium Borate buffer (pH-8) and 15 µL of 50 mM o-phthalaldehyde (solution in EtOH) was added at room temperature. The TCEP was added to ensure the cysteine remained in the free thiol form, as disulfide formation in the precursor was observed over time. The tube was then vortexed at room temperature for 30 seconds. Allowed to react for a further 45 minutes, after which a clear yellow solution was observed. At this point, the entire reaction mixture was injected directly into the HPLC system for immediate purification using Method D. The product peak was manually collected, immediately frozen and lyophilized (product tube was wrapped in foil) to yield a white powder (33% yield by area under the curve at 335 nm). HRMS (m/z) [M+H]$^+$ calcd. for C$_{39}$H$_{54}$N$_{10}$O$_{12}$SNa, 909.3541; found 909.3538.

FlICk Amanitin Modelling

A mol file of both FlICk amanitin variants was imported into Avagadro. Due to lack of 3D information in the file, the resulting structures were manipulated to roughly mimic the crystal structure of β-amanitin (the crosslink was pulled onto the same face of the macrocycle as in all known amatoxins, amides where made trans, etc.) The structures were then energy minimized using the MMF94s method with steepest decent gradient. The resulting structural models were imported into Mercury and images were captured.

FlICk Amanitin MTT Assay

Both FlICk amanitin and authentic α-amanitin (purchased from Sigma Aldrich) were dissolved in H$_2$O. The FlICk amanitin concentrations used were 100 µM, 20 µM, 4 µM, 0.8 µM, 0.16 µM, 0.032 µM, 0.0064 µM, 0.00128 µM. The α-amanitin concentrations used were 10 µM, 2 µM, 0.4 µM, 0.08 µM, 0.016 µM, 0.0032 µM, 0.00064 µM, 0.000128 µM, 0.0000256 µM. The cell culture and MTT assay procedures were carried out as per our report on the total synthesis of α-amanitin[38]. The MTT assays were run in triplicate. The IC50 assay curves were produced using Prism Software.

EXAMPLES

Various alternative embodiments and examples are described herein. These embodiments and examples are illustrative and should not be construed as limiting the scope of the invention.

Example 1: Melanocortin Analogs

We began our investigation of FlICk induction using commercially available OPA that was deployed in the cyclization of four linear α-MSH analogues based on the monocyclic Melanotan-II sequence. Notably, Melanotan-II [N-Acetyl-L-norleucyl-L-α-aspartyl-L-histidyl-D-phenylalanyl-L-arginyl-L-tryptophyl-L-lysinamide (2→7)-lactam], a very potent (K$_d$~1 nM) macrocyclic heptapeptide MSH analog[28], has been clinically trialed for erectile dysfunction[29] and is used illicitly to promote tanning. Nevertheless, apart from Melanotan-II, most monocyclic heptapeptide MSH analogs typically show much higher K$_d$ values (K$_d$>20 nM), which not only makes Melanotan-II unique among MSH analogs but underscores the synthetic challenges associated with generating high affinity heptapeptide MSH analogs[30]. Hence, four heptapeptides were synthesized with increasing length of the amine-bearing side chain:amino proprionic acid, amino-butyric acid, ornithine, and lysine (FIG. 2) to assess the effect of ring size in a competitive binding assay against Melanocortin Receptor 1 (MC1-R.)

Operationally, the reaction is especially user-friendly. The peptide, in the form of a lyophilized powder, is dissolved in borate buffer (pH 8), to which the o-phthalaldehyde, often isolated as a methyl-hemiacetal (see ESI) is added in EtOH along with a small amount of DMF to aid solubility. The combined solution is vortexed and the reaction mixture is directly subjected to resolution by HPLC. With 2 eq. of OPA at 10 mM, the reaction progress of FlICk induction was too fast to be accurately measured and the reaction was judged to be complete within 30 sec. The entire mixture is then loaded onto a standard C-18 SepPak or HPLC without further manipulation and the product peak is collected, frozen, and lyophilized. Peak-to-peak conversion was observed by HPLC (see supporting information) with yields ranging from (54-75%, beginning with linear peptides that were between 75 and 80% pure). Impressively, three of four FlICked MSH derivatives showed high affinity for MC1-R (Table 1). Evident from the results is the apparent need for a minimum ring size to achieve binding affinity comparable to the native α-MSH ($IC_{50}$=2.6 nM)[31]. One-carbon homologation of the DAP variant of the peptide results in an order of magnitude increase in binding affinity, while there appears to be an ideal ring size comprising ornithine as lysine substitution moderately diminishes binding affinity.

TABLE 1

Figure 2:
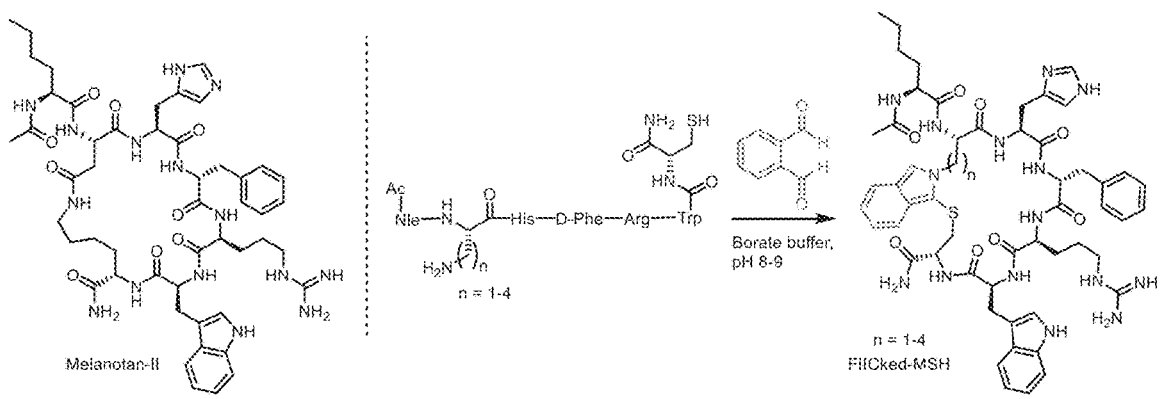
FIG. 2: At left: structure of Melanotan-II; At right: rapid, high yielding FlICk synthesis of α-MSH derivatives with different ring sizes.

Data for MSH derivatives prepared according to FIG. 2.

| MSH | $(CH_2)_n$ | Yield % | $K_i$ |
|---|---|---|---|
| A | n = 1 | 75 | 35 nM |
| B | n = 2 | 58 | 2.5 nM |
| C | n = 3 | 64 | 1.7 nM |
| D | n = 4 | 54 | 4.0 nM |

Figure 3:
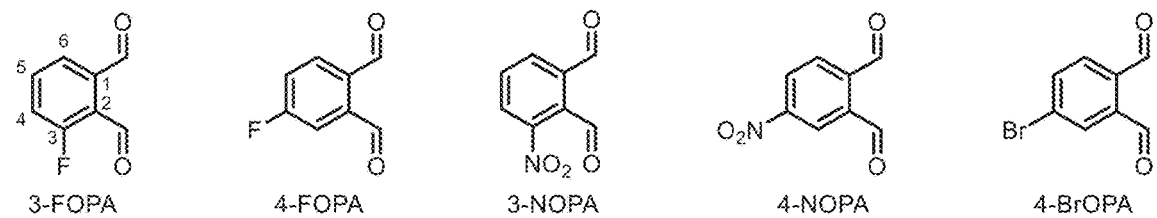
FIG. 3: Modified OPAs used in this study.

To access modified isoindoles with an eye to varying the absorbance and emission wavelengths, we synthesized five modified ortho-phthaldehydes (FIG. 3) by readily-accessible two- or three-step synthetic routes starting either with the corresponding xylene or phthalic acid (see ESI).

With these OPA derivatives in hand, we characterized the photophysical properties of the isoindoles that form quantitatively. Using the standard phthalaldehyde assay conditions for quantifying an amine via we added a known concentration of n-hexyl-amine (7 mM) and excess of OPA and NAc-cysteine to generate a known quantity of isoindole. Reaction progress was monitored by UV-vis spectroscopy; with the exception of the NOPAs, the reaction was judged to be complete within 30 seconds. Absorbance spectra were recorded and apparent molar extinction coefficients were calculated and compared to those of commercially available OPA, used as a standard, for which the quantum yield is known to be 0.47. Quantum yields were then measured accordingly (see ESI for detailed procedure). Results are reported in Table 2 in the context of FlICked MSH derivatives.

progress was monitored by recording the corresponding isoindole absorbance vs time). As expected, all five FlICked MSH derivatives showed similar Ki values (Table 1). FlICked MSH derivatives were found to be stable for over one month when stored at −20 deg. On standing in aqueous conditions, a small amount of unknown oxidized product $(M+16)^+$ was observed by ESI and was taken to likely resulted from reaction with molecular oxygen on the isoindole ring[32]. In addition, extended irradiation of the unmodified isoindole with UV-light or ambient sunlight led to observable photobleaching. By contrast, the electron-withdrawing substituents (F, $NO_2$) on the isoindole increase photostability and shelf-life, with the nitro derivatives greatly reducing unwanted oxidation at room temperature in aqueous solution (as observed by ESI mass spec.).

FlICked MSHs with fluoro-isoindoles exhibit vivid blue-green fluorescence (see graphical abstract) with spectral properties and quantum yields that are comparable to those of blue fluorescent proteins (BFPs).[33] While we had hoped that fluorescence could be exploited for visualizing MC1-R binding and internalization, the well-known background fluorescence due the over-production of melanin in melanocytes unfortunately impeded this application (data not shown).

Not surprisingly, isoindole formation on 3- and 4-substituted OPAs occurs with varying degrees of regioselectivity (see ESI) and, in certain cases the FlICked products were difficult to separate by standard reverse-phase HPLC. Nevertheless, in the case of the FlICk-MSH formed from 3-FOPA (Table 2, entry 1), two regio-isomeric FlICk products were readily separated in approximately 3:4 ratio based on the UV-absorbance at 280 nm (Trp absorbance). Both regioisomers show $A_{280\ nm}/A_{335\ nm}$ ratios that are within experimental error (~5%) thus demonstrating that both isoindoles have nearly identical molar extinction coefficients. In addition, each regioisomer shows nearly identical binding affinities (Table 2, entries 1a and 1b). While the apparent inseparability of these regioisomers may reflect a current limitation of this method, a similar limitation has arisen in certain instances where cis/trans alkene-stapled peptides are obtained as inseparable mixtures of cis/trans isomers[12c, 12d]. Notwithstanding such inconvenience, metal-mediated cross-metastasis is extensively pursued for stapling in biotechnology and medicine.

To expand the scope of this reaction, we reacted the other three linear MSH precursors (FIG. 1, where n=1,2,4) with

TABLE 2

Photophysical properties of modified isoindoles and $K_i$ values for corresponding MSHs constructed with modified OPAs. For entry-1, two regio-isomers (a and b) were separated and were found to have very similar $K_i$ values.

| Entry | OPA | $\lambda_{ex.}$ | $\lambda_{em.}$ | Stokes Shift | Φ | $K_i$ |
|---|---|---|---|---|---|---|
| 1 | 3-FOPA | 329 nm | 415 nm | 86 nm | 0.04 | a: 2.2 nM |
|   |        |        |        |       |      | b: 1.7 nM |
| 2 | 4-FOPA | 338 nm | 454 nm | 116 nm | 0.31 | 1.2 nM |
| 3 | 3-NOPA | 487 nm | NA | NA | <0.001 | 3.0 nM |
| 4 | 4-NOPA | 444 nm | NA | NA | <0.001 | 1.5 nM |
| 5 | 4-BrOPA | 345 nm | 452 nm | 116 nm | <0.001 | 1.6 nM |

Since MSH-C (FIG. 2) showed the highest affinity, the same linear precursor was condensed with these 5 new OPAs. FlICked MSH derivatives prepared from both FOPAs and the BrOPA formed within 30 seconds while those prepared from both NOPAs required approximately 15 min (reaction each of these OPAs to afford a focused library of HPLC-purified 20 MSHs (Table 3 and ESI for characterization). While affinities were not measured at this juncture, we were able to produce all 20 HPLC-purified peptides over the course of just two days, a feature that highlights both the facility and robustness of this reaction for use in applications of directed library development.

TABLE 3

Summary of FlICK MSH library. Yields are calculated by LC at 280 nm (tryptophan absorbance) as entire reaction mixture was directly subject to HPLC.

| $(CH_2)_n$ | 3-FOPA | 4-FOPA | 3-NOPA | 4-NOPA | 4-BrOPA |
|---|---|---|---|---|---|
| n = 1 | 73%* | 74% | 66%* | 47% | 49% |
| n = 2 | 60% | 55% | 71% | 62% | 39% |
| n = 3 | 77%* | 59% | 35% | 36% | 36% |
| n = 4 | 65%* | 53% | 39% | 28% | 29% |

Asterisks indicate combined yields of HPLC-separable regioisomers.

Example 2: Amatoxin Analogs

Figure 4:
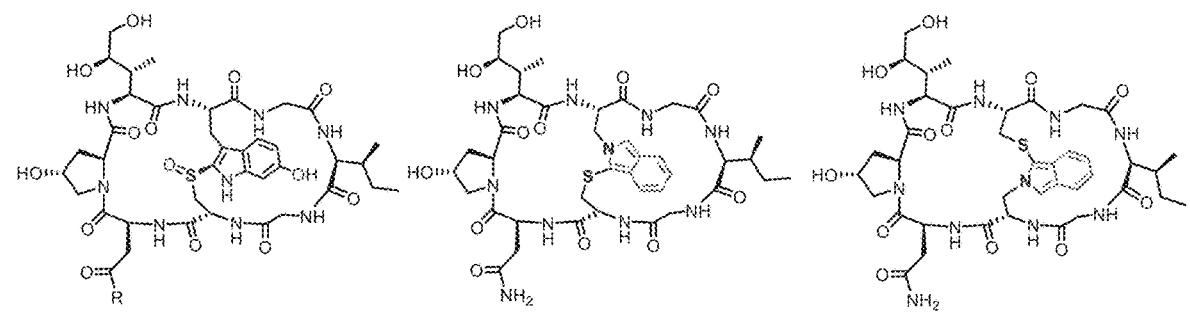
FIG. 4: At left: α/β-amanitins; middle: FlICk-amanitin-1; At right: FlICk-amanitin-2; each bicycle has the same overall connectivity of 5 intervening atoms in either the tryptathionine or isoindole crosslink.
Figure 4:
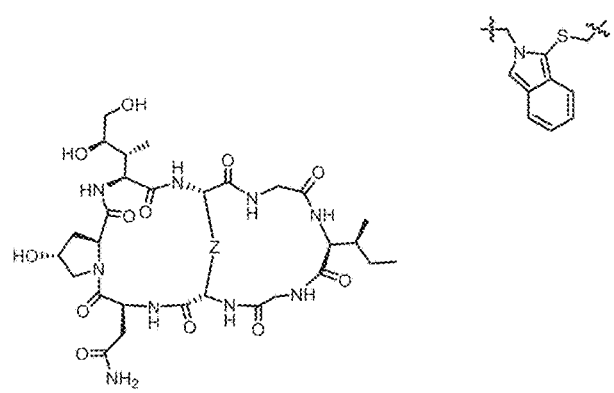

Given this preliminary success in FlICking a linear precursor to achieve a high-affinity monocyclic MSH analog, we applied this strategy to produce a challenging bicyclic peptide that was designed to mimic α-amanitin, a well-known cytotoxin. Both α- and β-amanitin (FIG. 4) possess a characteristic hydroxy-tryptathionine sulfoxide crosslink that rigidifies the macrocycle thereby restricting key orientations of the side chains which engage in significant interactions (H-bonding, hydrophobic) with the bridge helix of RNA Pol II. The indole of the tryptathionine crosslink engages in a 7-cation interaction with arginine-726 (A chain of RNA Polymerase) along with other hydrophobic interactions.[34] Whereas α-amanitin is cytotoxic to CHO cells ($IC_{50}$~0.5 µM), the synthetically accessible didexoy-derivative that lacks both the (R)-sulfoxide and the 6-hydroxy group on the tryptathionine is slightly less cytotoxic to CHO cells ($IC_{50}$~2 µM)[35].

We hypothesized that an isoindole, formed from DAP and cysteine, would serve as a fluorescent bio-isostere to replace the tryptathionine in α-amanitin, while retaining the same general connectivity in terms of the intra-annular distance between the two Cα carbons. In considering a FlICked amanitin analog, two possible isoindole orientations are conceivable given the circularly permutable nature of the peptide macrocycle as shown below in FIG. 4.

Molecular modelling and energy minimization on FlICked amanitin-1& -2 suggested that FlICk-amanitin-1 would adopt a structure that would be similar to β-amanitin for which a crystal structure is known[36] (note α-amanitin adopts a similar solution structure[37]). When compared with a crystal structure of β-amanitin, the gross structural features of the FlICk-amanitin-1 model appear similar. The tilt-angle of the indole relative to the macrolactam ring is similar whereby both indolyl crosslinks lie over the eastern ring of the molecule. Furthermore, the amide bonds appear to adopt a similar orientation, most notably in terms of the spatial arrangement of the cysteine NH, the asparagine NH and the carbonyl of $Gly^5$ which are suggested to be participating in hydrogen bonding per the modelling study. The most notable difference may be in the orientation on the amide bond between dihydroxyisoleucine and tryptophan/DAP and the orientation of the aspartate/asparagine side chain. By contrast, the modelled structure of FlICk-amanitin-2 appears grossly different from the crystal structure of β-amanitin; the isoindole now lies directly over the western ring of the molecule, veering out towards the viewer while the backbone structure appears contorted, particularly in the eastern j-turn.

Figure 5:
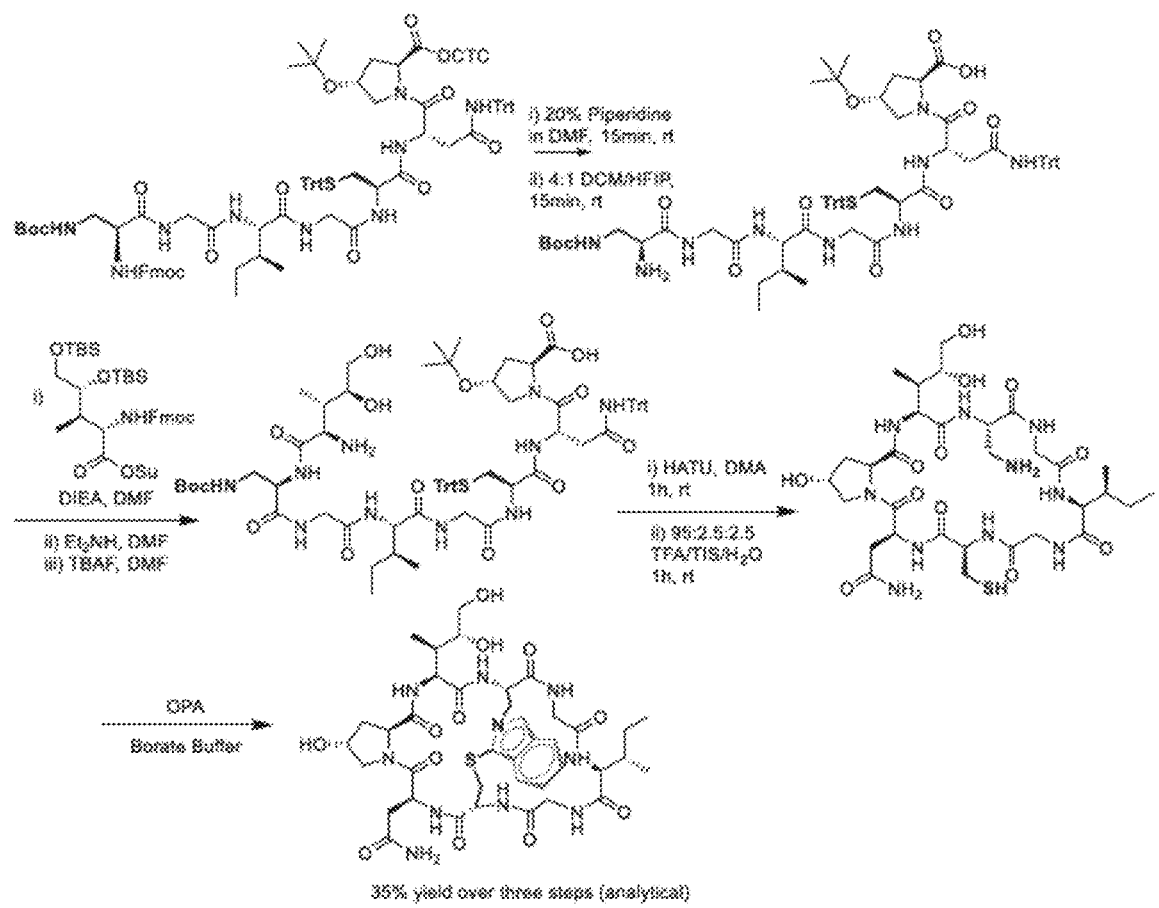
FIG. 5: Synthesis of the FlICk-amanitin-1.

Guided by this preliminary modelling, we readily synthesized FlICk-amanitin-1 in accord with the scheme shown in FIG. 5. Using a solid-phase synthesis strategy on 2-CTC resin with acid-labile side chain protection, the heptapeptide containing diaminoproprionic acids was synthesized on the solid phase. Following cleavage from the resin with mild acid (leaving the side chain functional groups concealed), the unnatural amino acid, dihydroxyisoleucine[38] was coupled to the heptapeptide in solution, which was then deprotected and cyclized with HATU in DMA. TFA treatment yielded a macrocycle, with the amine and thiol functionalities, primed for FlICk cyclization that was completed essentially upon mixing.

Figure 6:
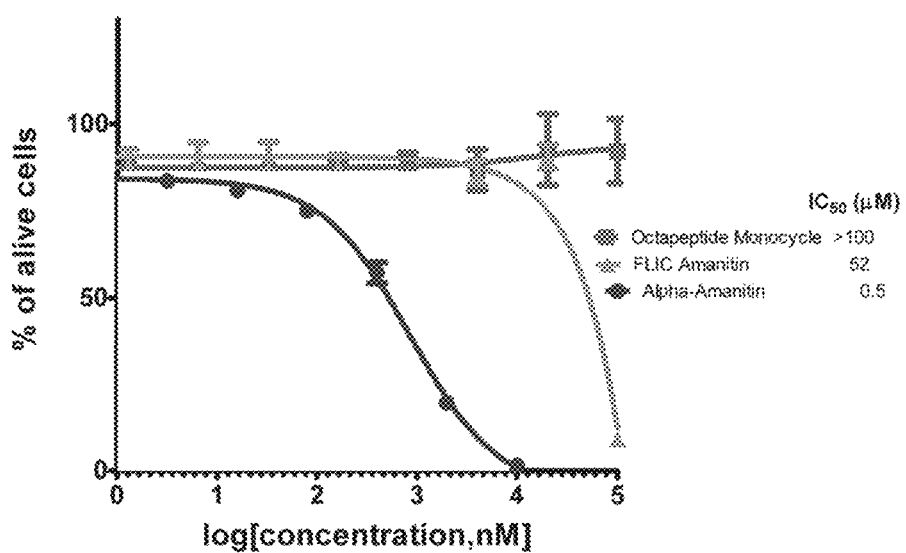
FIG. 6: Cytotoxicity assays—CHO cells were incubated with α-amanitin, the monocyclic octapeptide precursor and the FlICk-amanitin-1 for 72 h in triplicate and cell viability was assessed by spectrophotometry with MTT indicator.
Figure 7:
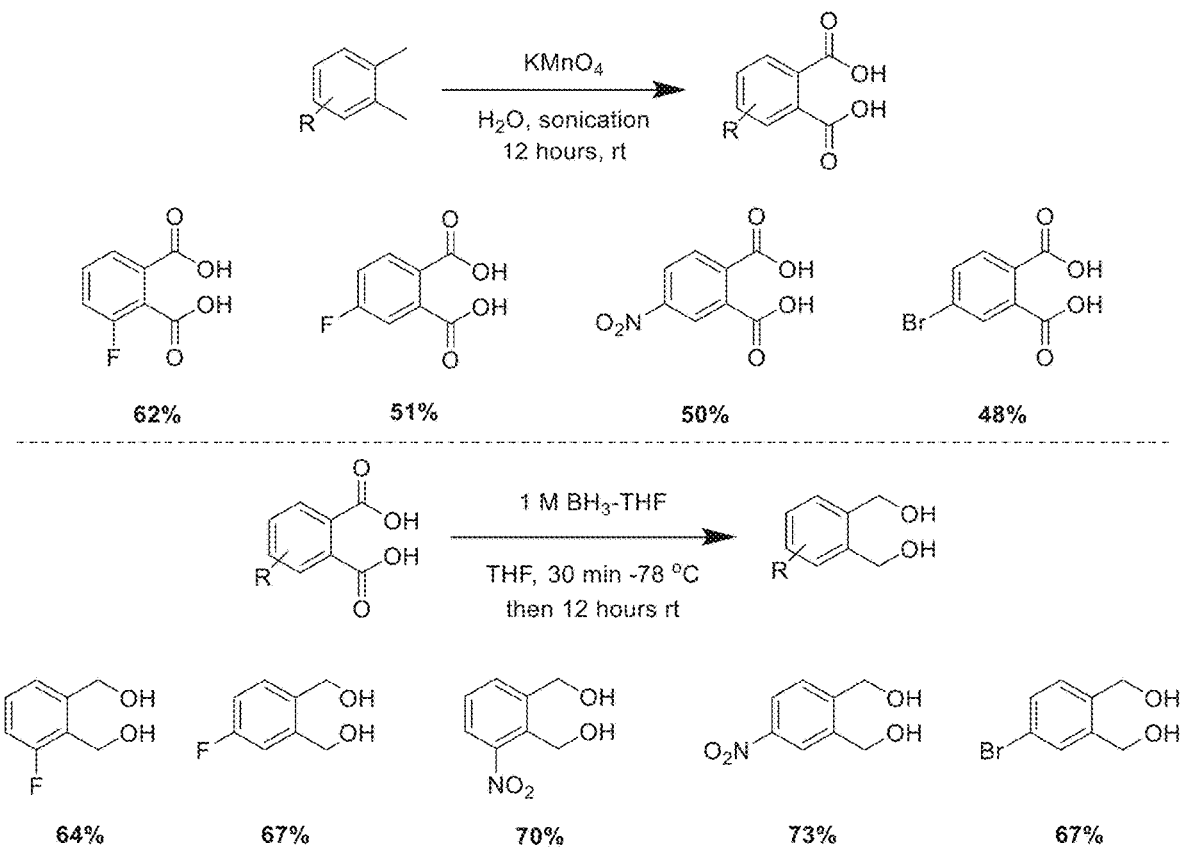
FIG. 7: Synthesis of Substituted o-Benzylic Diols. Permangate oxidation of substituted o-xlyenes under mild aqueous conditions followed by reduction of the resulting phthalic acids with $BH_3$-THF complex.
Figure 8:
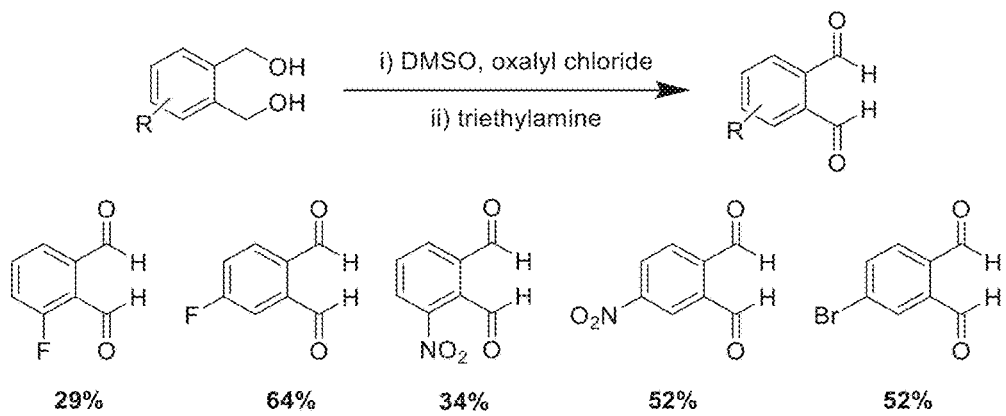
FIG. 8: Synthesis of Substituted o-Phthalaldehydes. Swern oxidation of o-benzylic diols yields o-phthalaldehyde derivatives that were isolated as methyl-hemiacetals due to their incompatibility with aqueous workup.
Figure 9:
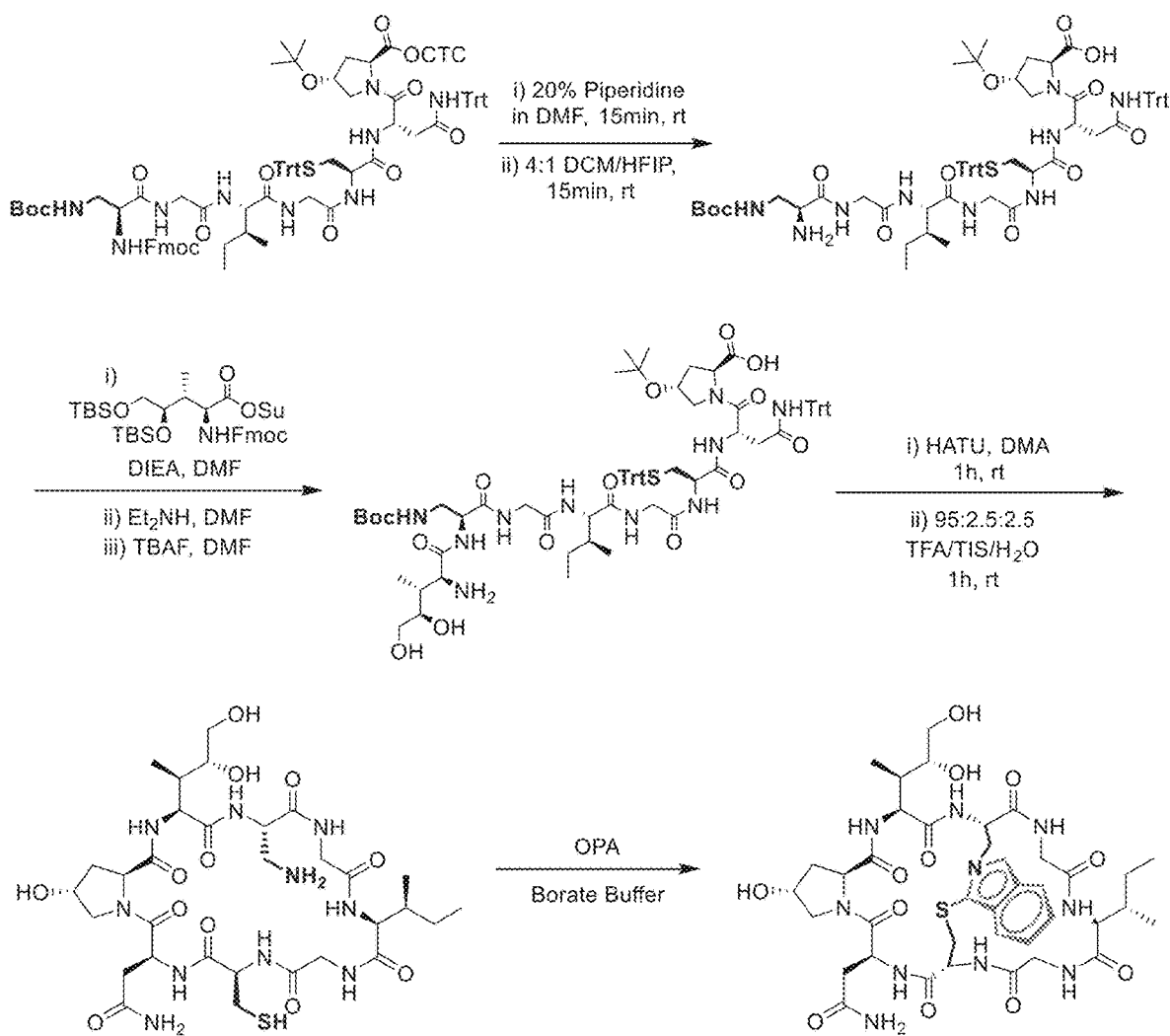
FIG. 9: Synthesis of Isoindole α-Amanitin Derivative. On resin synthesis of a linear octapeptide followed by mild acid cleavage to leave the protecting groups intact. Subsequent elaboration to a full length octapeptide followed by macrolactamization and global deprotection sets the stage for the ultimate step; intra-annular isoindole condensation. Synthesis of the protect dihydroxyisoleucine moiety was detailed in our previous report on the total synthesis of α-amanitin[10].
Figure 10A:
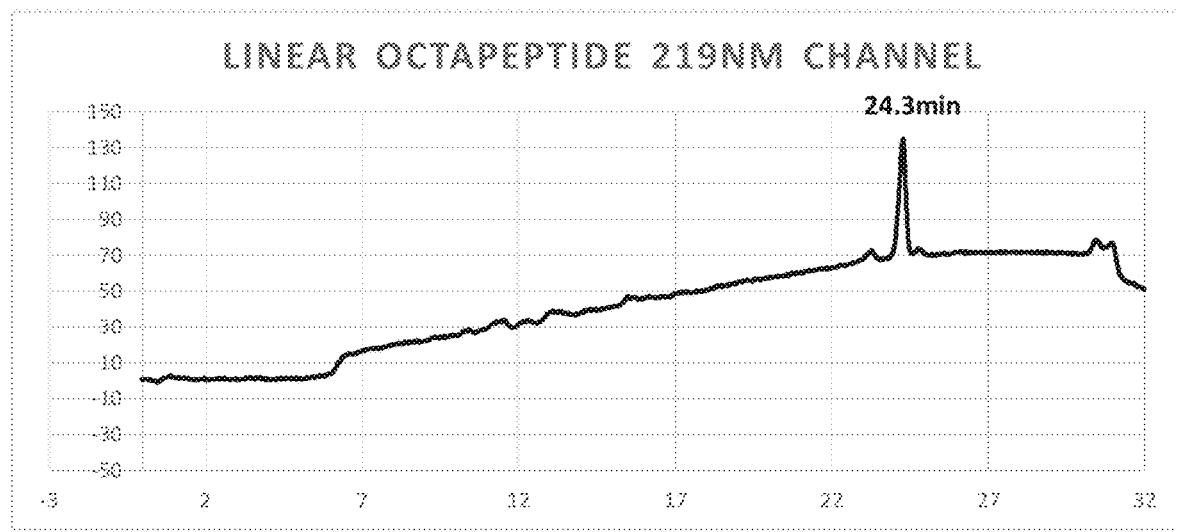
FIGS. 10A-10D: HPLC chromatographs for purified product reinjection. (A) linear octapeptide, 219 nm, $H_2N$-DhIle(Bis-O-TBS)-Dap(Boc)-Gly-Ile-Gly-Cys(Trt)-Asn(Trt)-Hyp(OtBu)-OH, 219 nm channel; (B) FlICk-amanitin, 230 nm channel; (C) FlICk-amanitin, 260 nm channel; (D) FlICk-amanitin, 335 nm channel.
Figure 10B:
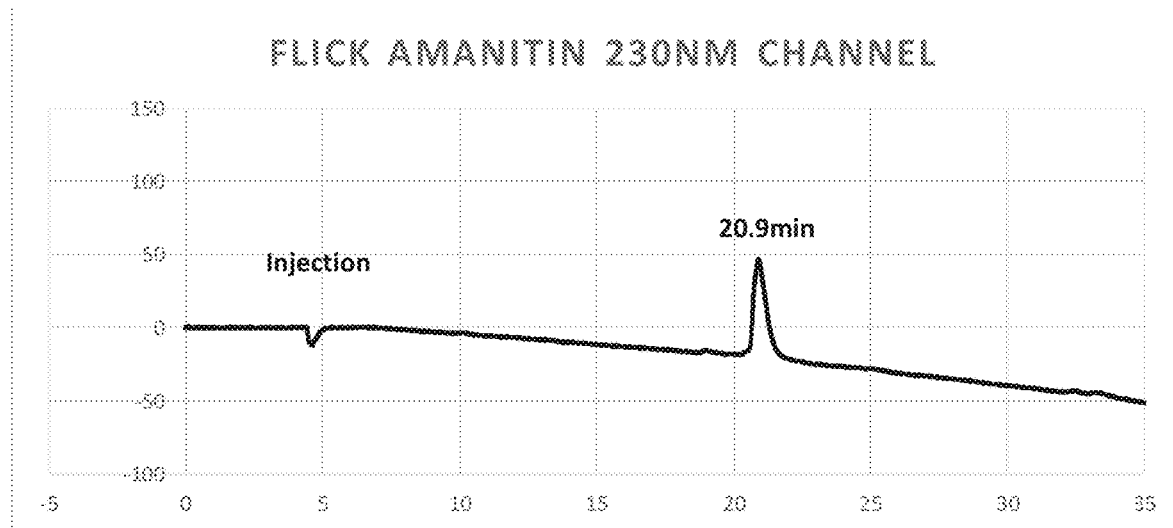
Figure 10C:
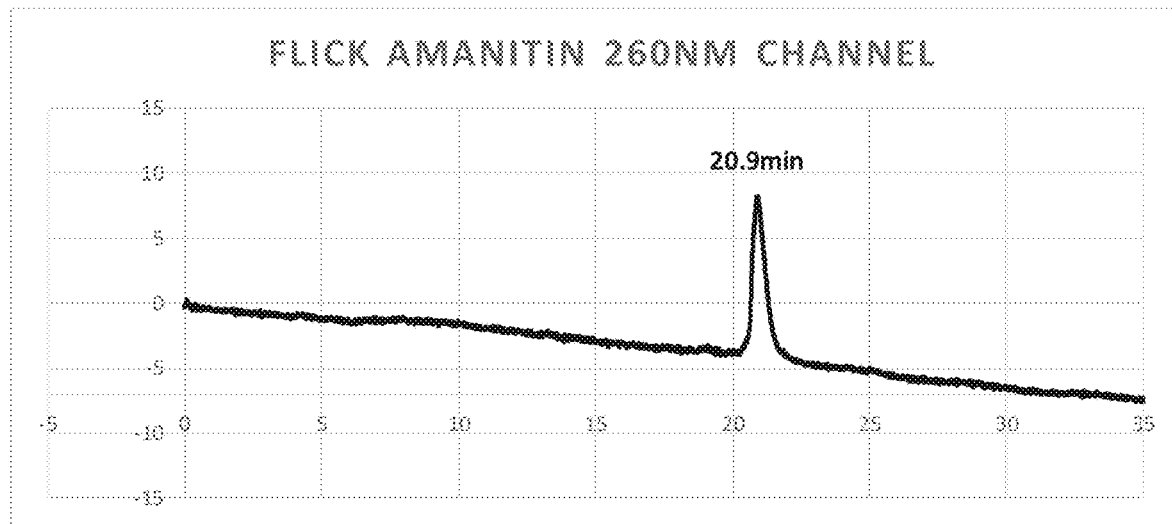
Figure 10D:
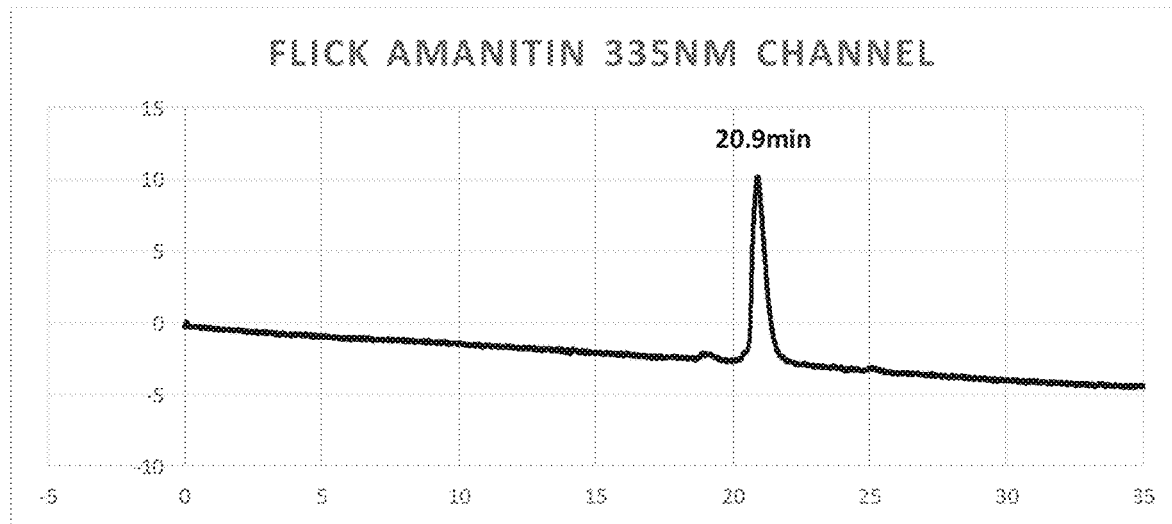
Figure 11A:
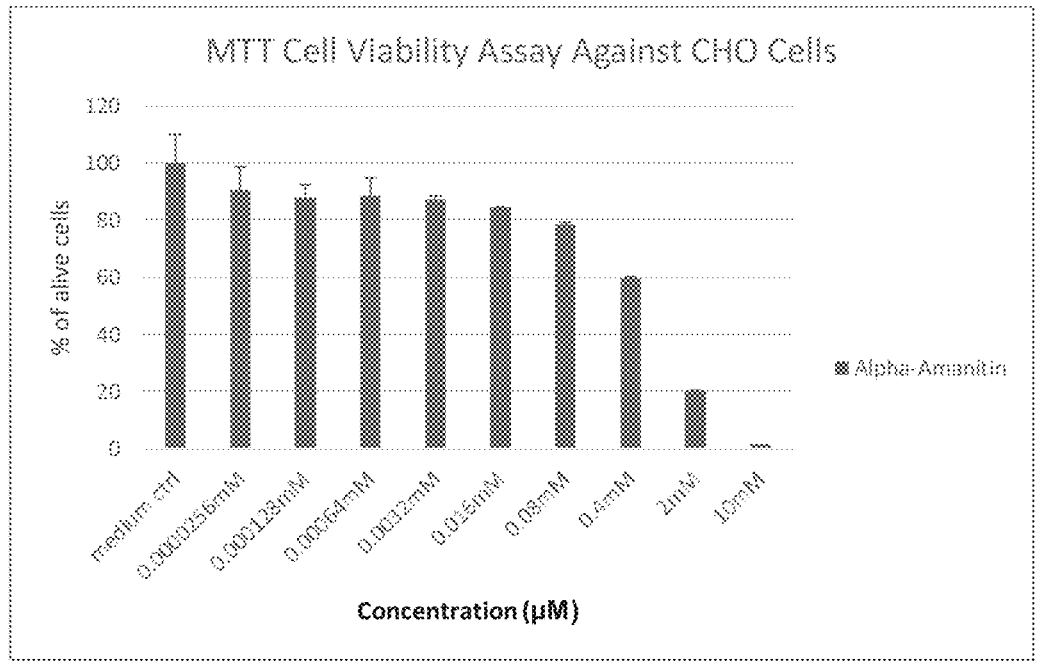
FIGS. 11A-11B: MTT cell viability assay against CHO cells: (A) alpha-amanitin; (B) FlICk-amanitin.
Figure 11B:
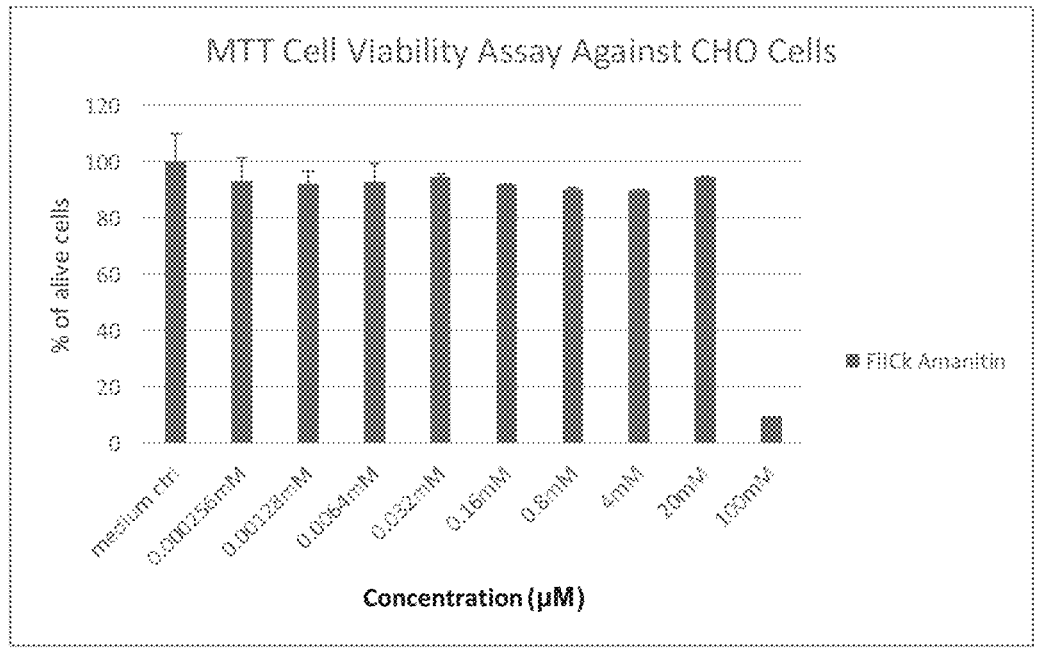
Figure 12:
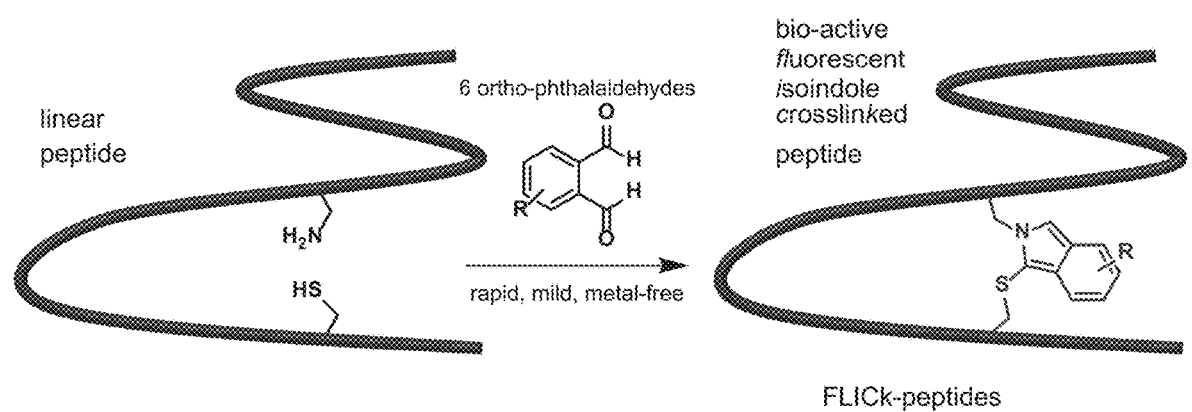
FIG. 12: Sketch illustrating the underlying crosslinking concept.

Whereas the monocyclic octapeptide precursor showed no detectable toxicity (data not shown), FlICk-amanitin-1 showed detectable toxicity at a level that is approximately 100-fold less toxic than that of α-amanitin (FIG. 6). Critically, FlICk-amanitin-1 is only 20-fold less toxic than dideoxy-amanitin ($IC_{50}$ of 2 µM), its more closely related congener. The diminished toxicity of FlICk-amanitin-1 may be understood in terms of a different orientation of the isoindole compared to the tryptathionine. Subtler differences in the intra-annular distances may also explain the reduced toxicity. Nevertheless, assuming that toxicity directly correlates with affinity for Pol II, a 20-fold difference in toxicity reflects less than 2 kcal/mol difference in binding energy. It is conceivable that further modification of the isoindole along with side-chain modifications may eventually provide for synthetic toxins of near-native toxicity. For the first time, a bioactive amanitin analog has been synthesized whereby the tryptathionine is replaced with a bio-orthogonal isoindole. This result now demonstrates that bicyclic peptides may be facilely re-engineered to with novel crosslinks for added bioactivity.

In conclusion, we have developed a methodology for rapidly accessing cross-linked fluorescent mono- and bicyclic peptides via the formation of a fluorescent isoindole crosslink. In so doing, we also developed a route to modified o-pthalaldehydes and measured the photophysical properties of the isoindoles they engender. We have applied this strategy to a clinically relevant peptide, α-MSH, and produced several high-affinity ligands with low single-digit nanomolar binding affinities. We then applied this strategy to a monocyclic peptide of no cytotoxicity to create a FlICked-bicycle that shows cytotoxicity and, which based on molecular modelling, structurally mimics α-amanitin, a highly toxic and medicinally relevant bicyclic peptide natural product. Taken together, these results demonstrate that this method may be a reliably augment bioactivity from inactive precursors. The utility of this approach lies in its high chemoselectivity, mild conditions, and operational simplicity. Someone skilled in the art may anticipate that OPAs could be further derivatized with azides, alkynes, biotin, or other reporter groups to increase the chemical functionality of FlICked peptides. Interestingly, FlICked peptides prepared from the FOPAs show vivid fluorescence blue-green with reasonable high quantum yields reminiscent of BFPs. We expect that the fluorescent nature of these peptides may enhance their value as probes in cell biology and for screening applications with built-in fluorescence. These findings portend success in applying FlICk synthesis to enhance the chance of discovering new bioactive mono- and bicyclic peptides from combinatorial arrays[39] and may possibly find additional utility for identifying cyclic peptides via phage display[40] and ribosome-display[16h], and for generating chemically constrained fluorescent proteins and antibody fragments.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to", and the word "comprises" has a corresponding meaning. As used herein, the singular forms "a", "an" and "the" include plural referents unless the context clearly dictates otherwise. Thus, for example, reference to "a thing" includes more than one such thing. Citation of references herein is not an admission that such references are prior art to an embodiment of the present invention. The invention includes all embodiments and variations substantially as hereinbefore described and with reference to the examples and drawings. Titles, headings, or the like are provided to enhance the reader's comprehension of this document, and should not be read as limiting the scope of the present invention.

REFERENCES

The entire disclosures of all applications, patents, and publications, cited above and below, are hereby incorporated by reference. However, it will be apparent to persons skilled in the art that a number of variations and modifications can be made without departing from the scope of the invention as defined in the claims. The reference to any prior art in this specification is not, and should not be taken as, an acknowledgement or any form of suggestion that that prior art forms part of the common general knowledge in Canada or any other country.

1. a) Craik D J, Fairlie D P, Liras S, Price D. The Future of Peptide-based Drugs. *Chem Biol Drug Des* 2013, 81(1): 136-147; b) Cardote T A F, Ciulli A. Cyclic and Macrocyclic Peptides as Chemical Tools To Recognise Protein Surfaces and Probe Protein-Protein Interactions. *ChemMedChem* 2016, 11(8): 787-794.
2. a) Fass D, Thorpe C. Chemistry and Enzymology of Disulfide Cross-Linking in Proteins. *Chem Rev* 2018, 118(3): 293-322; b) Chung B K W, Yudin A K. Disulfide-bridged peptide macrobicycles from nature. *Org Biomol Chem* 2015, 13(33): 8768-8779.
3. a) Craik D J, Daly N L, Waine C. The cystine knot motif in toxins and implications for drug design. *Toxicon* 2001, 39(1): 43-60; b) Wang C K, Craik D J. Designing macrocyclic disulfide-rich peptides for biotechnological applications. *Nat Chem Biol* 2018, 14(5): 417-427.
4. a) Willey J M, van der Donk W A. Lantibiotics: Peptides of diverse structure and function. *Annu Rev Microbiol* 2007, 61: 477-501; b) Ross A C, Liu H Q, Pattabiraman V R, Vederas J C. Synthesis of the Lantibiotic Lactocin S Using Peptide Cyclizations on Solid Phase. *J Am Chem Soc* 2010, 132(2): 462-463.
5. a) Wieland T, Faulstich H. Amatoxins, Phallotoxins, Phallolysin, and Antamanide—Biologically Active Components of Poisonous *Amanita* Mushrooms. *CRC Critical Reviews in Biochemistry* 1978, 5(3): 185-260; b) May J P, Perrin D M. Tryptathionine bridges in peptide synthesis. *Biopolymers* 2007, 88(5): 714-724; c) Hallen H E, Luo H, Scott-Craig J S, Walton J D. Gene family encoding the major toxins of lethal *Amanita* mushrooms. *Proc Natl Acad Sci USA* 2007, 104(48): 19097-19101.
6. Ma B, Banerjee B, Litvinov D N, He L W, Castle S L. Total Synthesis of the Antimitotic Bicyclic Peptide Celogentin C. *J Am Chem Soc* 2010, 132(3): 1159-1171.
7. Rodriguez L M D, Williams E T, Brimble M A. Chemical Synthesis of Bioactive Naturally Derived Cyclic Peptides Containing Ene-Like Rigidifying Motifs. *Chem-Eur J* 2018, 24(68): 17869-17880.
8. Cupido T, Tulla-Puche J, Spengler J, Albericio F. The synthesis of naturally occurring peptides and their analogs. *Curr Opin Drug Discov Dev* 2007, 10(6): 768-783.
9. a) Hill T A, Shepherd N E, Diness F, Fairlie D P. Constraining Cyclic Peptides To Mimic Protein Structure Motifs. *Angew Chem-Int Edit* 2014, 53(48): 13020-13041; b) Wojcik P, Berlicki L. Peptide-based inhibitors of protein-protein interactions. *Bioorg Med Chem Lett* 2016, 26(3): 707-713; c) Rhodes C A, Pei D H. Bicyclic Peptides as Next-Generation Therapeutics. *Chem-Eur J* 2017, 23(52): 12690-12703; d) Veber D F, Freidinger R M, Perlow D S, Paleveda W J, Holly F W, Strachan R G, et al. A Potent Cyclic Hexapeptide Analog of Somatostatin. *Nature* 1981, 292(5818): 55-58; e) Veber D F, Holly F W, Paleveda W J, Nutt R F, Bergstrand S J, Torchiana M, et al. Conformationally Restricted Bicyclic Analogs of Somatostatin. *Proc Natl Acad Sci USA* 1978, 75(6): 2636-2640.
10. a) Bock J E, Gavenonis J, Kritzer J A. Getting in Shape: Controlling Peptide Bioactivity and Bioavailability Using Conformational Constraints. *ACS Chem Biol* 2013, 8(3): 488-499; b) Gavenonis J, Sheneman B A, Siegert T R, Eshelman M R, Kritzer J A. Comprehensive analysis of loops at protein-protein interfaces for macrocycle design. *Nat Chem Biol* 2014, 10(9): 716-722.
11. Lau Y H, De Andrade P, Wu Y T, Spring D R. Peptide stapling techniques based on different macrocyclisation chemistries. *Chem Soc Rev* 2015, 44(1): 91-102.
12. a) Blackwell H E, Grubbs R H. Highly efficient synthesis of covalently cross-linked peptide helices by ring-closing metathesis. *Angew Chem-Int Edit* 1998, 37(23): 3281-3284; b) Cromm P M, Schaubach S, Spiegel J, Furstner A, Grossmann T N, Waldmann H. Orthogonal ring-closing alkyne and olefin metathesis for the synthesis of small GTPase-targeting bicyclic peptides. *Nature Communications* 2016, 7: 7; c) Hilinski G J, Kim Y W, Hong J, Kutchukian P S, Crenshaw C M, Berkovitch S S, et al. Stitched alpha-Helical Peptides via Bis Ring-Closing Metathesis. *J Am Chem Soc* 2014, 136(35): 12314-12322; d) Sousbie M, Vivancos M, Brouillette R L, Besserer-Offroy E, Longpre J M, Leduc R, et al. Structural Optimization and Characterization of Potent Analgesic Macrocyclic Analogues of Neurotensin (8-13). *J Med Chem* 2018, 61(16): 7103-7115.
13. a) Silvestri A P, Cistrone P A, Dawson P E. Adapting the Glaser Reaction for Bioconjugation: Robust Access to Structurally Simple, Rigid Linkers. *Angew Chem-Int Edit* 2017, 56(35): 10438-10442; b) Cistrone P A, Silvestri A P, Hintzen J C J, Dawson P E. Rigid Peptide Macrocycles from On-Resin Glaser Stapling. *ChemBioChem* 2018, 19(10): 1031-1035.
14. a) Meldal M, Tornoe C W. Cu-catalyzed azide-alkyne cycloaddition. *Chem Rev* 2008, 108(8): 2952-3015; b) Angell Y, Burgess K. Ring closure to beta-turn mimics via copper-catalyzed azide/alkyne cycloadditions. *J Org Chem* 2005, 70(23): 9595-9598; c) Beierle J M, Horne W S, van Maarseveen J H, Waser B, Reubi J C, Ghadiri M R. Conformationally Homogeneous Heterocyclic Pseudotetrapeptides as Three-Dimensional Scaffolds for Rational Drug Design: Receptor-Selective Somatostatin Analogues. *Angew Chem-Int Edit* 2009, 48(26): 4725-4729; d) Ingale S, Dawson P E. On Resin Side-Chain Cyclization of Complex Peptides Using CuAAC. *Org Lett* 2011, 13(11): 2822-2825; e) Li H Y, Aneja R, Chaiken I. Click Chemistry in Peptide-Based Drug Design. *Molecules* 2013, 18(8): 9797-9817.
15. Frost J R, Scully C C G, Yudin A K. Oxadiazole grafts in peptide macrocycles. *Nat Chem* 2016, 8(12): 1105-1111.
16. a) Brunel F M, Dawson P E. Synthesis of constrained helical peptides by thioether ligation: application to analogs of gp41. *Chem Commun* 2005(20): 2552-2554; b) Spokoyny A M, Zou Y K, Ling J J, Yu H T, Lin Y S, Pentelute B L. A Perfluoroaryl-Cysteine SNAr Chemistry Approach to Unprotected Peptide Stapling. *J Am Chem Soc* 2013, 135(16): 5946-5949; c) Assem N, Ferreira D J, Wolan D W, Dawson P E. Acetone-Linked Peptides: A Convergent Approach for Peptide Macrocyclization and Labeling. *Angew Chem-Int Edit* 2015, 54(30): 8665-8668; d) Aimetti A A, Shoemaker R K, Lin C C, Anseth K S. On-resin peptide macrocyclization using thiol-ene click chemistry. *Chem Commun* 2010, 46(23): 4061-4063; e) Zhao B C, Zhang Q Z, Li Z G. Constructing thioether-tethered cyclic peptides via on-resin intra-molecular thiol-ene reaction. *J Pept Sci* 2016, 22(8): 540-544; f) Tian Y, Li J X, Zhao H, Zeng X Z, Wang D Y, Liu Q S, et al. Stapling of unprotected helical peptides via photoinduced intramolecular thiol-yne hydrothiolation. *Chem Sci* 2016, 7(5): 3325-3330; g) Wang Y X, Chou D H C. A Thiol-Ene Coupling Approach to Native Peptide Stapling and Macrocyclization. *Angew Chem-Int Edit* 2015, 54(37): 10931-10934; h) Goto Y, Ohta A, Sako Y, Yamagishi Y, Murakami H, Suga H. Reprogramming the translation initiation for the synthesis of physiologically stable cyclic peptides. *ACS Chem Biol* 2008, 3(2): 120-129.
17. Qin T, Cornella J, Li C, Malins L R, Edwards J T, Kawamura S, et al. A general alkyl-alkyl cross-coupling enabled by redox-active esters and alkylzinc reagents. *Science* 2016, 352(6287): 801-805.
18. a) Mendive-Tapia L, Preciado S, Garcia J, Ramon R, Kielland N, Albericio F, et al. New peptide architectures through C—H activation stapling between tryptophan-phenylalanine/tyrosine residues. *Nature Communications* 2015, 6: 9; b) Brown S P, Smith A B. Peptide/Protein Stapling and Unstapling: Introduction of s-Tetrazine, Photochemical Release, and Regeneration of the Peptide/Protein. *J Am Chem Soc* 2015, 137(12): 4034-4037; c) Zhang C, Vinogradova E V, Spokoyny A M, Buchwald S L, Pentelute B L. Arylation Chemistry for Bioconjugation. *Angewandte Chemie (International ed in English)* 2018.
19. Tala S R, Singh A, Lensing C J, Schnell S M, Freeman K T, Rocca J R, et al. 1,2,3-Triazole Rings as a Disulfide Bond Mimetic in Chimeric AGRP-Melanocortin Peptides: Design, Synthesis, and Functional Characterization. *ACS Chem Neurosci* 2018, 9(5): 1001-1013.
20. a) Roth M. Fluorescence Reaction for Amino Acids. *Anal Chem* 1971, 43(7): 880-882; b) Benson J R, Hare P E. Ortho-Phthalaldehyde—Fluorogenic Detection of Primary Amines in Picomole Range—Comparison with Fluorescamine and Ninhydrin. *Proc Natl Acad Sci USA* 1975, 72(2): 619-622; c) Chen R F, Scott C, Trepman E. Fluorescence Properties of Ortho-Phthalaldehyde Derivatives of Amino Acids. *Biochim Biophys Acta* 1979, 576 (2): 440-455; d) Lee K S, Drescher D G. Fluorometric Amino-Acid-Analysis with Ortho-Phthaldehyde. *Int J Biochem* 1978, 9(7): 457-467; e) Ishida Y, Fujita T, Asai K. New Detection and Separation Method for Amino-Acids by High-Performance Liquid-Chromatography. *J Chromatogr* 1981, 204(JAN): 143-148; f) Puri R N, Roskoski R. Reaction of Low-Molecular Weight Aminothiols with o-Phthalaldehyde. *Anal Biochem* 1988, 173 (1): 26-32.
21. a) Matteucci G, Lanzara V, Ferrari C, Hanau S, Bergamini C M. Active site labeling of erythrocyte transglutaminase by o-phthalaldehyde. *Biol Chem* 1998, 379(7): 921-924; b) Puri R N, Bhatnagar D, Roskoski R. Inactivation of Yeast Hexokinase by Ortho-Phthaladehyde—Evidence for the Presence of a Cysteine and a Lysine at or Near the Active-Site. *Biochim Biophys Acta* 1988, 957(1): 34-46.
22. a) Simons S S, Thompson E B, Johnson D F. Fluorescent Chemoaffinity Labeling—Potential Application of a New Affinity Labeling Technique to Glucocorticoid Receptors. *Biochemistry* 1979, 18(22): 4915-4922; b) Portoghese P S, El Kouhen R, Law P Y, Loh H H, Le Bourdonnec B. Affinity labels as tools for the identification of opioid receptor recognition sites. *Farmaco* 2001, 56(3): 191-196.
23. a) Maly D J, Allen J A, Shokat K M. A mechanism-based cross-linker for the identification of kinase-substrate pairs. *J Am Chem Soc* 2004, 126(30): 9160-9161; b) Statsuk A V, Maly D J, Seeliger M A, Fabian M A, Biggs W H, Lockhart D J, et al. Tuning a Three-Component Reaction For Trapping Kinase Substrate Complexes. *J Am Chem Soc* 2008, 130(51): 17568-17574.
24. a) Morineau G, Azoulay M, Frappier F. Reaction of o-phthalaldehyde with Amino Acids and Glutathione—Application to High Performance Liquid-Chromatogrphay Determination. *J Chromatogr* 1989, 467(1): 209-216; b) Yan C C, Huxtable R J. Fluorometric-Determination of Monobromobimane and o-Phthalaldehyde Adducts of Gamma-Glutaminylcysteine and Glutathione—Application to Assay Gamma-Glutaminylcysteinyl Synthetase-Activity and Glutathione Concentration in Liver. *J Chromatogr B-Biomed Appl* 1995, 672(2): 217-224.
25. Holder J R, Haskell-Luevano C. Melanocortin ligands: 30 years of structure-activity relationship (SAR) studies. *Med Res Rev* 2004, 24(3): 325-356.
26. a) Raposinho P D, Correia J D G, Oliveira M C, Santos I. Melanocortin-1 Receptor-Targeting With Radiolabeled Cyclic alpha-Melanocyte-Stimulating Hormone Analogs for Melanoma Imaging. *Biopolymers* 2010, 94(6): 820-829; b) Zhang C, Zhang Z, Lin K-S, Lau J, Zeisler J, Colpo N, et al. Melanoma Imaging Using 18F-Labeled alpha-Melanocyte-Stimulating Hormone Derivatives with Positron Emission Tomography. *Mol Pharm* 2018, 15(6): 2116-2122.
27. Zhang C C, Lin K S, Benard F. Molecular Imaging and Radionuclide Therapy of Melanoma Targeting the Melanocortin 1 Receptor. *Mol Imaging* 2017, 16: 15.
28. Alobeidi F, Castrucci A M D, Hadley M E, Hruby V J. Potent and Prolonged Acting Cyclic Lactam Analogs of Alpha-Melanotropin—Design Based on Molecular Dynamics. *J Med Chem* 1989, 32(12): 2555-2561.
29. a) Dorr R T, Lines R, Levine N, Brooks C, Xiang L, Hruby V J, et al. Evaluation of Melanotan-II, a superpotent cyclic melanotropic peptide in a pilot phase-I clinical study. *Life Sci* 1996, 58(20): 1777-1784; b) Wessells H, Fuciarelli K, Hansen J, Hadley M E, Hruby V J, Dorr R, et al. Synthetic melanotropic peptide initiates erections in men with psychogenic erectile dysfunction: Double-blind, placebo controlled crossover study. *J Urol* 1998, 160(2): 389-393.

30. a) Mayorov A V, Han S Y, Cai M Y, Hammer M R, Trivedi D, Hruby V J. Effects of macrocycle size and rigidity on melanocortin receptor-1 and -5 selectivity in cyclic lactam alpha-melanocyte-stimulating hormone analogs. *Chem Biol Drug Des* 2006, 67(5): 329-335; b) Ericson M D, Freeman K T, Schnell S M, Haskell-Luevano C. A Macrocyclic Agouti-Related Proteini/Nle (4),DPhe(7) alpha-Melanocyte Stimulating Hormone Chimeric Scaffold Produces Subnanoniolar Melanocortin Receptor Ligands. *J Med Chem* 2017, 60(2): 805-813.
31. Yang Y K, Dickinson C, HaskellLuevano C, Gantz I. Molecular basis for the interaction of Nle(4),D-Phe(7) melanocyte stimulating hormone with the human melanocortin-1 receptor (melanocyte alpha-MSH receptor). *J Biol Chem* 1997, 272(37): 23000-23010.
32. Stobaugh J F, Repta A J, Sternson L A. Autoxidation of 1-(tert-butylthio)-2-(N-propyl)isoindole. *J Org Chem* 1984, 49(22): 4306-4309.
33. a) Hein R, Tsien R Y. Engineering green fluorescent protein for improved brightness, longer wavelengths and fluorescence resonance energy transfer. *Curr Biol* 1996, 6(2): 178-182; b) Ai H W, Shaner N C, Cheng Z H, Tsien R Y, Campbell R E. Exploration of new chromophore structures leads to the identification of improved blue fluorescent proteins. *Biochemistry* 2007, 46(20): 5904-5910; c) Subach O M, Gundorov I S, Yoshimura M, Subach F V, Zhang J H, Gruenwald D, et al. Conversion of Red Fluorescent Protein into a Bright Blue Probe. *Chem Biol* 2008, 15(10): 1116-1124.
34. Bushnell D A, Cramer P, Kornberg R D. Structural basis of transcription: alpha-Amanitin-RNA polymerase II cocrystal at 2.8 A resolution. *Proc Natl Acad Sci USA* 2002, 99(3): 1218-1222.
35. a) Faulstich H, Trischmann H, Wieland T, Wulf E. Ether Derivatives of Alpha-Amanitin—Introduction of Spacer Moieties, Lipophilic Residues and Radioactive Labels. *Biochemistry* 1981, 20(22): 6498-6504; b) Wieland T, Gotzendorfer C, Dabrowski J, Lipscomb W N, Shoham G. Unexpected Similarity of the Structures of the Weakly Toxic Amanitin (S)-Sulfoxide and the Highly Toxic (R)-Sulfoxide and Sulfone as Revealed by Proton Nuclear Magnetic-Resonance and X-Ray Analysis. *Biochemistry* 1983, 22(5): 1264-1271.
36. a) Kostansek E C, Lipscomb W N, Yocum R R, Thiessen W E. Crystal-Structure of Mushroom Toxin Beta-Amanitin. *J Am Chem Soc* 1977, 99(4): 1273-1274; b) Kostansek E C, Lipscomb W N, Yocum R R, Thiessen W E. Conformation of Mushroom Toxin Beta-Amanitin in Crystalline State. *Biochemistry* 1978, 17(18): 3790-3795.
37. Tonelli A E, Patel D J, Wieland T, Faulstich H. Structure of Alpha-Amanitin in Dimethylsulfoxide Solution. *Biopolymers* 1978, 17(8): 1973-1986.
38. Matinkhoo K, Pryyma A, Todorovic M, Patrick B O, Perrin D M. Synthesis of the Death-Cap Mushroom Toxin alpha-Amanitin. *J Am Chem Soc* 2018, 140(21): 6513-6517.
39. Martinez-Ceron M C, Giudicessi S L, Saavedra S L, Gurevich-Messina J M, Erra-Balsells R, Albericio F, et al. Latest Advances in OBOC Peptide Libraries. Improvements in Screening Strategies and Enlarging the Family From Linear to Cyclic Libraries. *Curr Pharm Biotechnol* 2016, 17(5): 449-457.
40. a) Oneil K T, Hoess R H, Jackson S A, Ramachandran N S, Mousa S A, Degrado W F. Identification of Novel Peptide Antagonists for GPIIB/IIIA from a Conformationally Constrained Phage Peptide Library. *Proteins* 1992, 14(4): 509-515; b) Heinis C, Rutherford T, Freund S, Winter G. Phage-encoded combinatorial chemical libraries based on bicyclic peptides. *Nat Chem Biol* 2009, 5(7): 502-507; c) Ng S, Jafari M R, Derda R. Bacteriophages and Viruses as a Support for Organic Synthesis and Combinatorial Chemistry. *ACS Chem Biol* 2012, 7(1): 123-138; d) Kalhor-Monfared S, Jafari M R, Patterson J T, Kitov P I, Dwyer J J, Nuss J M, et al. Rapid biocompatible macrocyclization of peptides with decafluorodiphenylsulfone. *Chem Sci* 2016, 7(6): 3785-3790.

What is claimed is:

1. A compound comprising a cyclic peptide of Formula IIb wherein: Formula IIb has the structure:

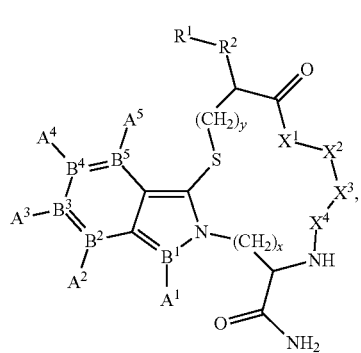

(Formula IIb)

wherein:

$R^1$ is —Ac or —H;

$R^2$ is -Nle-;

$X^1$ is -His- or -D-His-;

$X^2$ is -Phe- or -D-Phe-;

$X^3$ is -Arg- or -D-Arg-;

$X^4$ is -Trp- or -D-Trp-;

$A^1$, $A^2$, $A^3$, $A^4$ and $A^5$, are each independently, hydrogen, halogen, $NO_2$, CN, alkyne, azide, aryl, heteroaryl, COOH, $SO_3^-$, $CF_3$, RCO, CONHR, $NH_2$, NHR, $NR_2$, ether, thioether, hydroxyl, or boronate;

R is an alkyl or an alkenyl, each of which is optionally substituted;

$B^1$, $B^2$, $B^3$, $B^4$ and $B^5$, are each independently, carbon or nitrogen; and x and y, are each independently, a natural number between 1-15.

* * * * *